(12) United States Patent
Klemarczyk

(10) Patent No.: US 9,969,690 B2
(45) Date of Patent: May 15, 2018

(54) CURE ACCELERATORS FOR ANAEROBIC CURABLE COMPOSITIONS

(71) Applicant: Henkel IP & Holding GmbH, Duesseldorf (DE)

(72) Inventor: Philip T. Klemarczyk, Canton, CT (US)

(73) Assignee: Henkel IP & Holding GmbH, Duesseldorf (DE)

(*) Notice: Subject to any disclaimer, the term of this patent is extended or adjusted under 35 U.S.C. 154(b) by 0 days. days.

(21) Appl. No.: 15/452,768

(22) Filed: Mar. 8, 2017

(65) Prior Publication Data

US 2017/0174630 A1 Jun. 22, 2017

Related U.S. Application Data

(63) Continuation of application No. PCT/US2015/053068, filed on Sep. 30, 2015.
(Continued)

(51) Int. Cl.
*C08F 2/00* (2006.01)
*C08F 20/06* (2006.01)
(Continued)

(52) U.S. Cl.
CPC .......... *C07D 215/06* (2013.01); *C07C 227/26* (2013.01); *C07C 229/18* (2013.01);
(Continued)

(58) Field of Classification Search
CPC .......... C08K 5/16; C08L 33/06; C07D 209/22; C07D 209/24; C07D 215/06; C07C 211/48
(Continued)

(56) References Cited

U.S. PATENT DOCUMENTS 3,093,632 A * 6/1963 Mull .................... C07D 209/44
540/476
3,218,305 A 11/1965 Krieble
(Continued)

FOREIGN PATENT DOCUMENTS

CN 103113247 5/2013
DE 1 817 989 12/1976
(Continued)

OTHER PUBLICATIONS

International Search Report issued in connection with International Application No. PCT/US2015/053068 dated Jan. 28, 2016.
(Continued)

*Primary Examiner* — William K Cheung
(74) *Attorney, Agent, or Firm* — Steven C. Bauman

(57) ABSTRACT

Cure accelerators for anaerobic curable compositions, such as adhesives and sealants, are provided, and which are defined with reference to the compounds shown in structure I

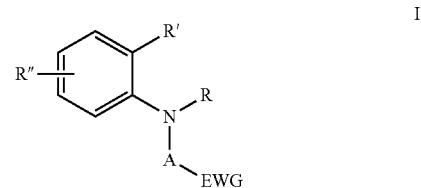

where A is $CH_2$ or benzyl, R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or
(Continued)

alkenylene-ether, alkylene (meth)acrylate, carbonyl, carboxyl, nitroso, sulfonate, hydroxyl or haloalkyl, and EWG is as shown, an electron withdrawing group, such as nitro, nitrile, carboxylate or trihaloalkyl.

11 Claims, 10 Drawing Sheets

Related U.S. Application Data

(60) Provisional application No. 62/058,201, filed on Oct. 1, 2014, provisional application No. 62/142,606, filed on Apr. 3, 2015.

(51) Int. Cl.

| | | |
|---|---|---|
| *C08F 118/02* | (2006.01) | |
| *C07D 215/06* | (2006.01) | |
| *C08F 20/28* | (2006.01) | |
| *C08K 5/3437* | (2006.01) | |
| *C07D 209/08* | (2006.01) | |
| *C08K 5/3417* | (2006.01) | |
| *C07C 255/25* | (2006.01) | |
| *C08K 5/315* | (2006.01) | |
| *C07C 253/30* | (2006.01) | |
| *C07C 229/18* | (2006.01) | |
| *C08K 5/18* | (2006.01) | |
| *C07C 227/26* | (2006.01) | |

(52) U.S. Cl.
CPC .......... *C07C 253/30* (2013.01); *C07C 255/25* (2013.01); *C07D 209/08* (2013.01); *C08F 20/28* (2013.01); *C08K 5/18* (2013.01); *C08K 5/315* (2013.01); *C08K 5/3417* (2013.01); *C08K 5/3437* (2013.01)

(58) Field of Classification Search
USPC ...................................... 526/222, 317.1, 319
See application file for complete search history.

(56) References Cited

U.S. PATENT DOCUMENTS

| | | | |
|---|---|---|---|
| 3,970,505 | A | 7/1976 | Hauser et al. |
| 4,180,640 | A | 12/1979 | Doherty et al. |
| 4,259,462 | A | 3/1981 | Nakano et al. |
| 4,287,330 | A | 9/1981 | Rich |
| 4,321,349 | A | 3/1982 | Rich |
| 5,411,988 | A | 5/1995 | Bockow et al. |
| 5,605,999 | A | 2/1997 | Chu et al. |
| 5,811,473 | A | 9/1998 | Ramos et al. |
| 6,391,993 | B1 | 5/2002 | Attarwala et al. |
| 6,583,289 | B1 | 6/2003 | McArdle et al. |
| 6,835,762 | B1 | 12/2004 | Kelmarczyk et al. |
| 6,897,277 | B1 | 5/2005 | Klemarczyk et al. |
| 6,958,368 | B1 | 10/2005 | Klemarczyk et al. |
| 8,362,112 | B2 | 1/2013 | Birkett et al. |
| 8,481,659 | B2 | 7/2013 | Birkett et al. |
| 2002/0042534 | A1 | 4/2002 | Murahashi et al. |
| 2012/0129994 | A1* | 5/2012 | Birkett ................ C08F 290/067 524/239 |

FOREIGN PATENT DOCUMENTS

| | | |
|---|---|---|
| DE | 2 806 701 | 8/1978 |
| FR | 1581361 | 9/1969 |
| JP | 07-308757 | 11/1995 |

OTHER PUBLICATIONS

Duen-Ren Hou et al.; Formation of 4,5,6,7-Tetrahydroisoindoles by Palladium-Catalyzed Hydride Reduction J. Org. Chem. 2007, 72, 9231-9239, Scheme 4, p. 9239.

Lukevics Edmunds et al.; "Synthesis and Neurotropic Activity of Novel Quinoline Derivatives", Molecules 1997, 2, 180-185, Scheme 3, p. 183-184.

R.D. Rich, "Anaerobic Adhesives" in Handbook of Adhesive Technology, 29, 467-79, A. Pizzi and K. L. Mittal, eds., Marcel Dekker, Inc., New York (1994).

* cited by examiner

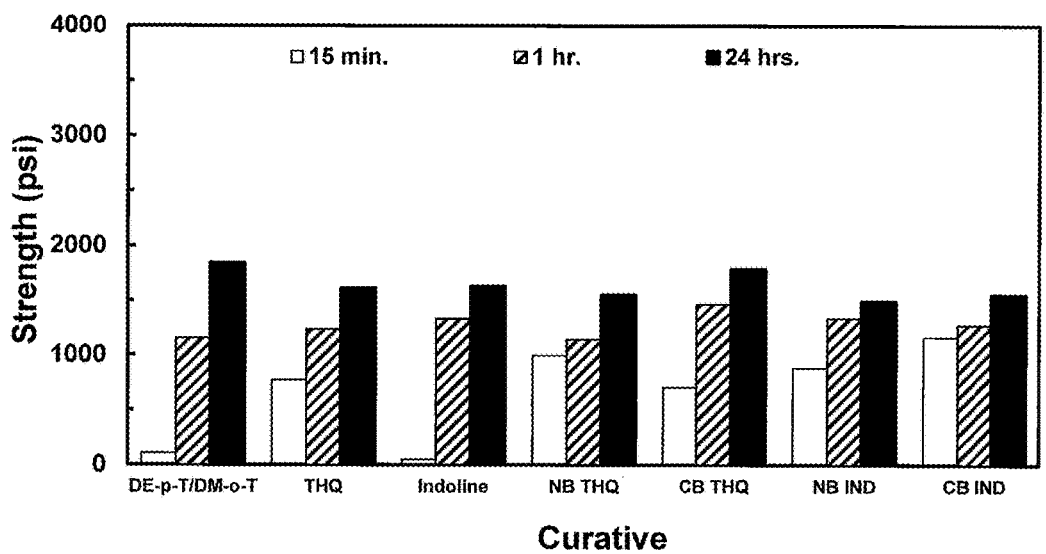
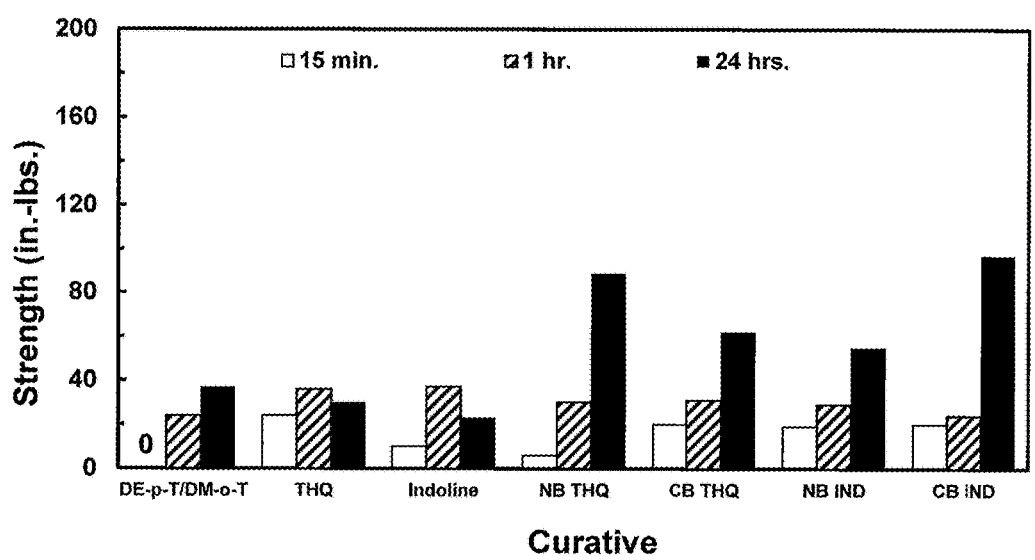

CURE ACCELERATORS FOR ANAEROBIC CURABLE COMPOSITIONS

This application is a continued application of PCT/US2015/053068 filed Sep. 30, 2015, which claims benefit of provisional application 62/058,201 filed Oct. 1, 2014 and claims benefit of provisional application of 62/142,606 filed Apr. 3, 2015, where the contents of which are incorporated herein by reference.

BACKGROUND

Field

Cure accelerators for anaerobic curable compositions, such as adhesives and sealants, are provided, and which are defined with reference to the compounds shown in structure I

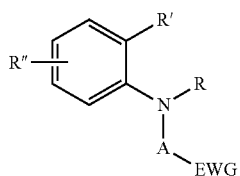

where A is $CH_2$ or benzyl, R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is as shown, an electron withdrawing group, such as nitro, nitrile, carboxylate or trihaloalkyl.

Brief Description of Related Technology

Anaerobic adhesive compositions generally are well-known. See e.g. R. D. Rich, "Anaerobic Adhesives" in *Handbook of Adhesive Technology*, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), and acetyl phenylhydrazine ("APH") with maleic acid. See e.g. U.S. Pat. No. 3,218,305 (Krieble), U.S. Pat. No. 4,180,640 (Melody), U.S. Pat. No. 4,287,330 (Rich) and U.S. Pat. No. 4,321,349 (Rich).

Saccharin and APH are used as standard cure accelerator components in anaerobic adhesive cure systems. Indeed, many of the LOCTITE-brand anaerobic adhesive products currently available from Henkel Corporation use either saccharin alone or both saccharin and APH. These chemicals have scrutinized in certain parts of the world, and thus efforts have been undertaken to identify candidates as replacements.

Examples of other curatives for anaerobic adhesives include thiocaprolactam [e.g., U.S. Pat. No. 5,411,988)] and thioureas [e.g., U.S. Pat. No. 3,970,505 (Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-308,757 (acyl, alkyl, alkylidene, alkylene and alkyl thioureas)], certain of the latter of which had been used commercially up until about twenty years ago.

Trithiadiaza pentalenes have also been shown to be effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

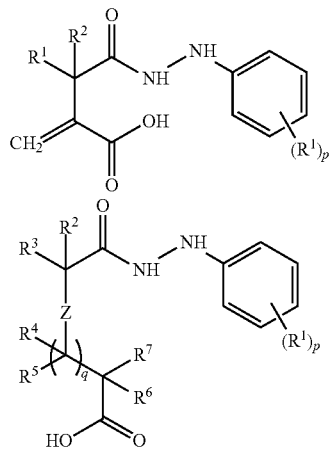

where $R^1$-$R^7$ are each independently selected from hydrogen and $C_{1-4}$; Z is a carbon-carbon single bond or carbon-carbon double bond; q is 0 or 1; and p is between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure

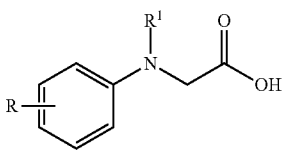

where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and alkaryl, an example of which is phenyl glycine and N-methyl phenyl glycine.

U.S. Pat. No. 6,958,368 (Messana) provides an anaerobic curable composition. This composition is based on a (meth) acrylate component with an anaerobic cure-inducing composition substantially free of saccharin and within the following structure

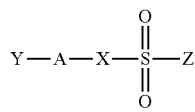

where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Three Bond Co. Ltd., Tokyo, Japan has in the past described as a component in anaerobic adhesive and sealant compositions a component called tetrahydroquinoline ("THQ").

And more recently Henkel Corporation has demonstrated the efficacy of new cure accelerators. The first class is within the structure below

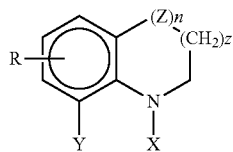

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1 and z is 1-3, provided that when X is H, z is not 2 and is preferably 1. More specifically, THQ-based or indoline-based adducts may be embraced thereby. (See U.S. Pat. No. 8,481,659.)

The second class is within the structure below

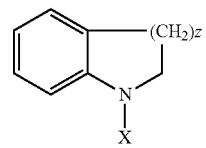

where X is $C_{1-20}$ alkyl, $C_{2-20}$ alkenyl, or $C_{7-20}$ alkaryl, any of which may be interrupted by one or more hereto atoms, and which are functionalized by at least one and preferably at least two groups selected from —OH, —NH$_2$ or —SH and z is 1-3. (See U.S. Pat. No. 8,362,112.)

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in conventional anaerobic cure inducing compositions have to one degree or another come under regulatory scrutiny, alternative components for anaerobic cure inducing compositions would be desirable. Accordingly, it would be desirable to identify new materials that function as cure components in the cure of anaerobically curable compositions.

SUMMARY

Cure accelerators for anaerobic curable compositions, such as adhesives and sealants, are provided as another option to satisfy that desire.

The compounds useful as cure accelerators for anaerobic curable compositions are defined with reference to structure I:

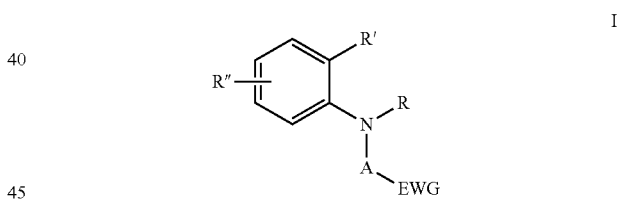

where A is CH$_2$ or benzyl, R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is as shown, an electron withdrawing group, such as nitro, nitrile, carboxylate or trihaloalkyl.

Compounds within structure I may be prepared from the following starting material II:

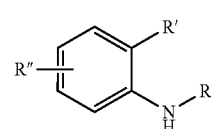

where R, R' and R" are as described above.

Compounds within structure I may be prepared in the general reaction scheme as follows:

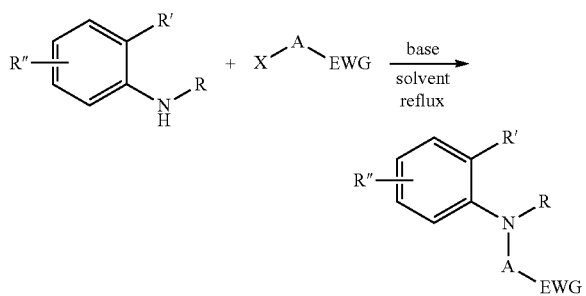

where A, R, R', R" and EWG are as described above.

More specifically, the reaction schemes may be represented as follows:

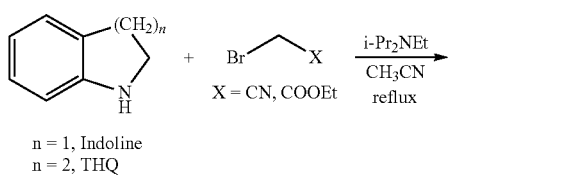

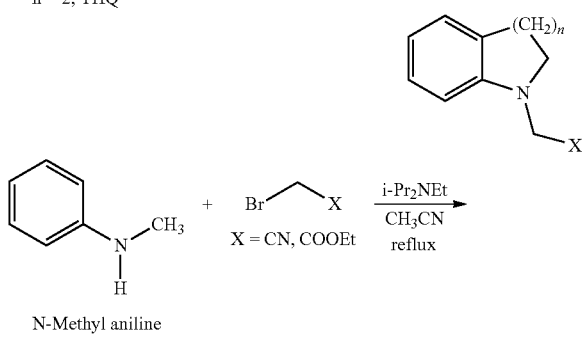

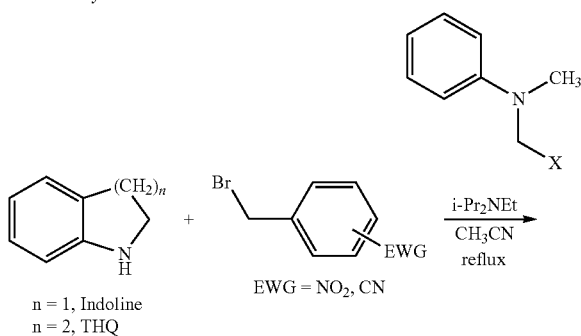

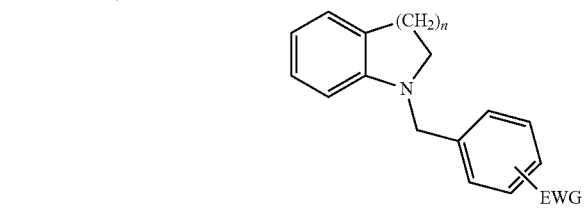

where n is 1 or 2 in the top scheme and X is a representative electron withdrawing group as shown. While an electron withdrawing group-containing alkyl (such as methyl) or benzyl bromide is shown as the reactant in this scheme, other halides and other leaving groups such as tosylate and mesylate, may be used as well.

Methods of preparing and using anaerobically curable compositions prepared with the cure accelerators within structure I also are provided, as well are the reaction products of the anaerobically curable compositions.

In addition, compounds within structure I are also provided.

BRIEF DESCRIPTION OF THE FIGURES

FIG. 15 depicts a plot of tensile strength vs. cure time of the anaerobic adhesive composition (Formulation 1), some of which using the inventive cure accelerators and others using conventional ones, on steel pins and collars.

FIG. 16 depicts a plot of break strength vs. cure time of the anaerobic adhesive composition (Formulation 2), some of which using the inventive cure accelerators and others using conventional ones, on steel nuts and bolts.

DETAILED DESCRIPTION

Figure 1:
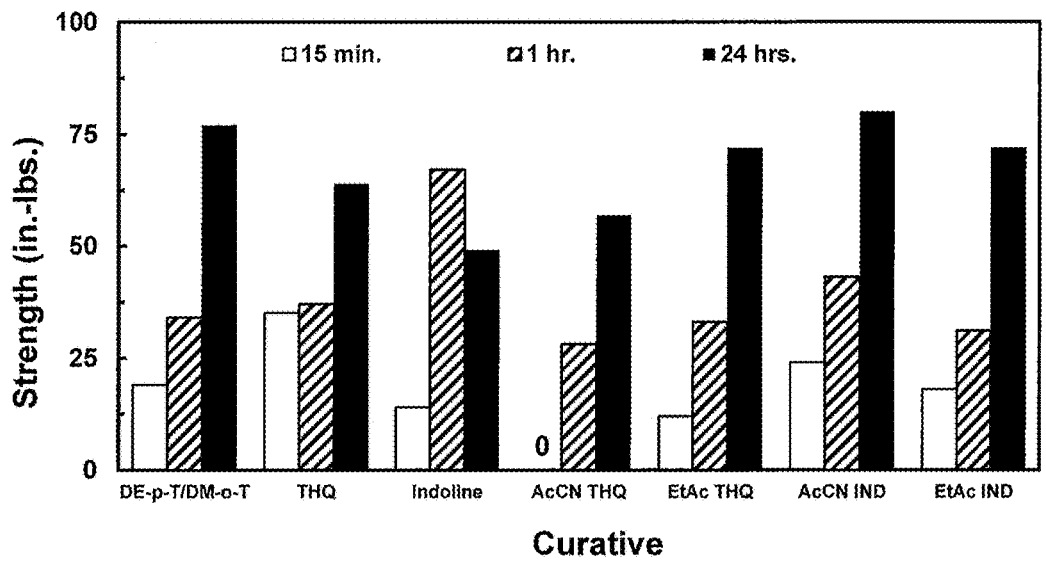
FIG. 1 depicts a plot of break strength vs. cure time of the anaerobic adhesive composition (Formulation 1), some of which using the inventive cure accelerators and others using conventional ones, on steel nuts and bolts.

As noted above, cure accelerators for anaerobic curable compositions, such as adhesives and sealants, are provided, and which are defined with reference to the compound shown in structure I.

The addition of such compounds as cure accelerators into anaerobic curable compositions as a replacement for some or all of the amount of conventional anaerobic cure accelerators (such as the toluidines, DE-p-T and DM-o-T, and/or APH) and indoline, surprisingly develops ultimate adhesive properties, while are comparable to those observed from conventional anaerobic curable compositions.

Cure accelerators for anaerobic curable compositions, such as adhesives and sealants, are provided, and which are defined with reference to the compound shown in structure I

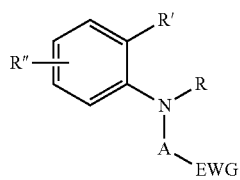

where A is $CH_2$ or benzyl, R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is as shown, an electron withdrawing group, such as nitro, nitrile, carboxylate or trihaloalkyl.

Specific examples of compounds within structure I are:

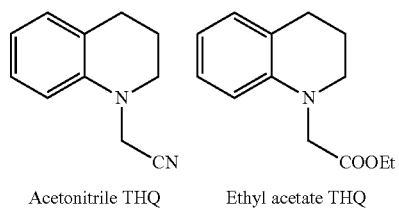

Acetonitrile THQ     Ethyl acetate THQ

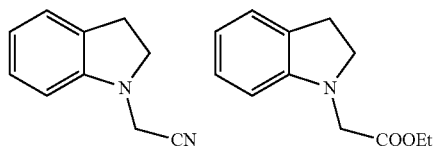

Acetonitrile IND     Ethyl acetate IND

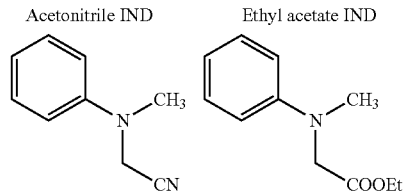

Acetonitrile NMA     Ethyl acetate NMA

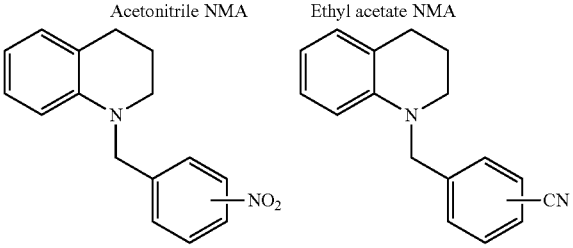

Nitrobenzyl THQ     Cyanobenzyl THQ

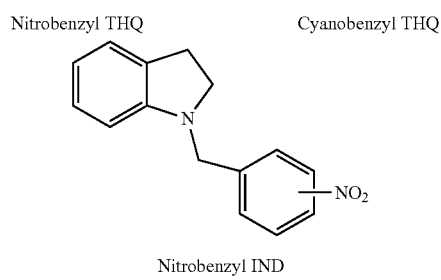

Nitrobenzyl IND

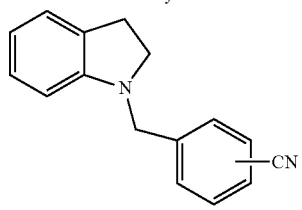

Cyanobenzyl IND

As noted above, compounds within structure I may be prepared from the following starting material II:

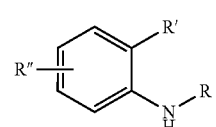

where R, R', and R" are as described above.

Examples of these compounds within structure II include:

Tetrahydroquinoline
(THQ)

Indoline
(IND)

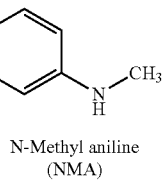
N-Methyl aniline
(NMA)

Compounds within structure I may be thus prepared in the general reaction scheme as follows:

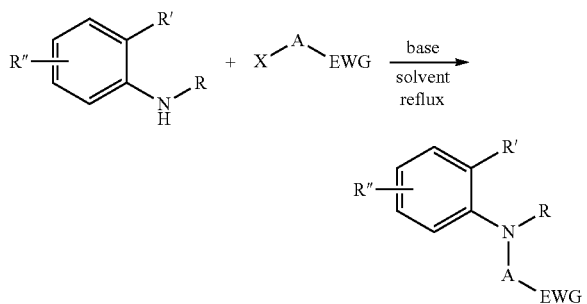

where A, R, R', R" and EWG are as described above, and X is leaving group, such as a halogen, desirably bromine, tosylate or mesylate.

More specifically, the reaction schemes may be represented as follows:

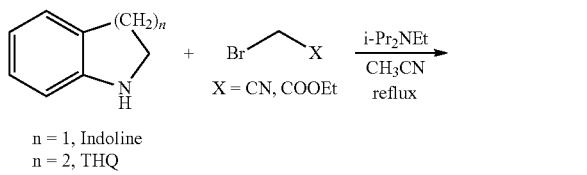

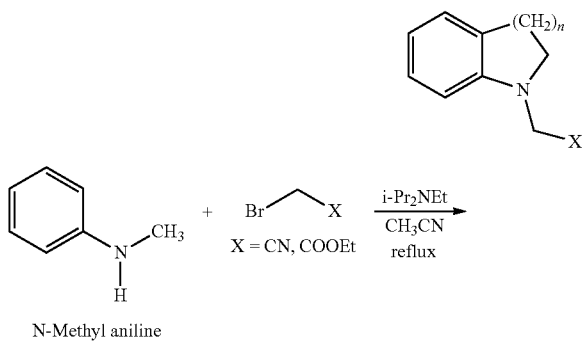

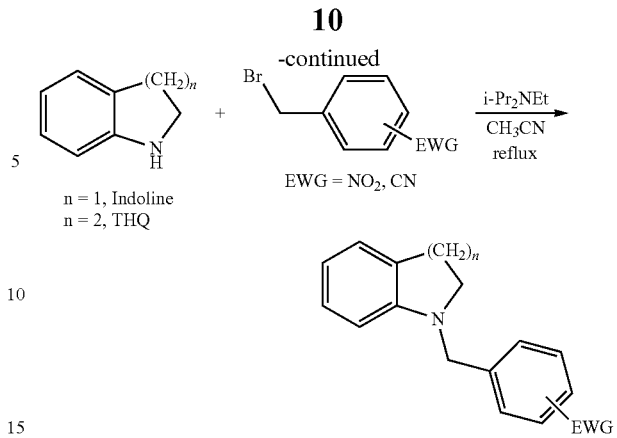

where n is 1 or 2 in the top scheme and X is a representative electron withdrawing group as shown. While an electron withdrawing group-containing alkyl (such as methyl) or benzyl bromide is shown as the reactant in this scheme, other halides or other leaving groups such as tosylate or mesylate, may be used as well.

In preparing the compounds of structure I, the reaction may be conducted in the presence of a solvent, in which case the compound of structure II may be dissolved in solvent prior to reaction with the alkyl halide, or vice versa.

The temperature employed in the reaction may also vary over a wide range. Where the components are combined in approximately chemical equivalent amounts or with one in slight excess over the other, useful temperatures may vary from room temperature or below, e.g., 10° C. to 15° C., up to and including temperatures of 100° C.

The so-formed compounds may be purified to remove impurities, such as reaction by-products or impurities that accompany the reactants. The compounds can be purified for example by distillation, filtration, stripping, chromatography, or recrystallization, such that the purified reaction product(s) are essentially free of impurities, or comprise less than about 1 weight percent of impurities.

Anaerobic curable compositions generally are based on a (meth)acrylate component, together with an anaerobic cure-inducing composition. In the present invention, the anaerobic cure-inducing composition, has at least reduced levels of APH or toluidines (such as about 50% or less by weight of that which is used in conventional anaerobic curable compositions, for instance less than about 10 weight percent, such as less than about 5 weight percent, and desirably less than about 1 weight percent) or is free of APH or toluidines altogether. In place of some or all of APH or toluidines is the inventive cure accelerator—that is, compounds embraced by structure I.

(Meth)acrylate monomers suitable for use as the (meth) acrylate component in the present invention may be selected from a wide variety of materials, such as those represented by $H_2C=CGCO_2R^{10}$, where G may be hydrogen, halogen or alkyl groups having from 1 to about 4 carbon atoms, and $R^{10}$ may be selected from alkyl, cycloalkyl, alkenyl, cycloalkenyl, alkaryl, alkaryl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di- or tri-functional (meth)acrylates such as polyethylene glycol di(meth)acrylates, tetrahydrofuran (meth) acrylates and di(meth)acrylates, hydroxypropyl (meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth) acrylates, diglycerol tetra(meth)acrylates, tetramethylene di(meth)acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula

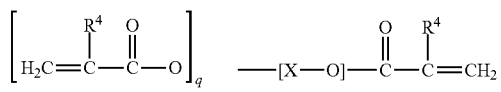

where $R^4$ is a radical selected from hydrogen, halogen or alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, such as desirably 30, and desirably about 20.

For example, X can be an organic radical of the formula:

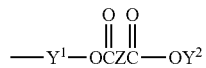

where each of $Y^1$ and $Y^2$ is an organic radical, such as a hydrocarbon group, containing at least 2 carbon atoms, and desirably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Oligomers with (meth)acrylate functionality may also be used. Examples of useful (meth)acrylate-functionalized oligomers include those having the following general formula:

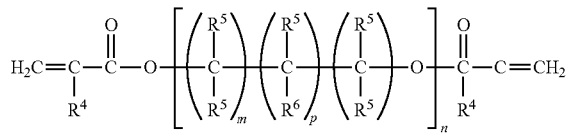

where $R^5$ represents a radical selected from hydrogen, lower alkyl of from 1 to about 4 carbon atoms, hydroxy alkyl of from 1 to about 4 carbon atoms, or

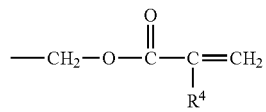

where $R^4$ is a radical selected from hydrogen, halogen, or lower alkyl of from 1 to about 4 carbon atoms; $R^6$ is a radical selected from hydrogen, hydroxyl, or

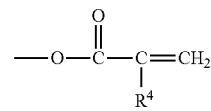

m is an integer equal to at least 1, e.g., from 1 to about 15 or higher, and desirably from 1 to about 8; n is an integer equal to at least 1, e.g., 1 to about 40 or more, and desirably between about 2 and about 10; and p is 0 or 1.

Typical examples of acrylic ester oligomers corresponding to the above general formula include di-, tri- and tetraethyleneglycol dimethacrylate; di(pentamethyleneglycol)dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from labile hydrogen, heterocyclic ring, hydroxy, amino, cyano, and halo polar groups. Typical examples of compounds within this category are cyclohexylmethacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of materials are the reaction product of (meth)acrylate-functionalized, hydroxyl- or amino-containing materials and polyisocyanate in suitable proportions so as to convert all of the isocyanate groups to urethane or ureido groups, respectively. The so-formed (meth)acrylate urethane or urea esters may contain hydroxy or amino functional groups on the nonacrylate portion thereof. (Meth)acrylate esters suitable for use have the formula

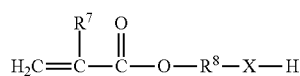

where X is selected from —O— and

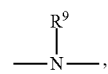

where $R^9$ is selected from hydrogen or lower alkyl of 1 through 7 carbon atoms; $R^7$ is selected from hydrogen, halogen (such as chlorine) or alkyl (such as methyl and ethyl radicals); and $R^8$ is a divalent organic radical selected from lower alkylene of 1 through 8 carbon atoms, phenylene and naphthylene. These groups upon proper reaction with a polyisocyanate, yield a monomer of the following general formula:

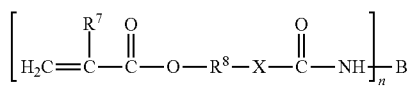

where n is an integer from 2 to about 6; B is a polyvalent organic radical selected from alkyl, alkenyl, cycloalkyl, cycloalkenyl, aryl, alkaryl, alkaryl and heterocyclic radicals both substituted and unsubstituted, and combinations thereof; and $R^7$, $R^8$ and X have the meanings given above.

Depending on the nature of B, these (meth)acrylate esters with urea or urethane linkages may have molecular weights placing them in the oligomer class (such as about 1,000 up to about 5,000) or in the polymer class (such as about greater than 5,000).

Of course, combinations of these (meth)acrylate monomers may also be used.

The (meth)acrylate component may comprise from about 10 to about 90 percent by weight of the composition, such as about 60 to about 90 percent by weight, based on the total weight of the composition.

Additional components have in the past been included in traditional anaerobic adhesive and/or sealant compositions to alter the physical properties of either the formulation or the reaction products thereof. For instance, one or more of thermal resistance-conferring co-reactants (such as maleimide components), diluent components reactive at elevated temperature conditions, mono- or poly-hydroxyalkanes, polymeric plasticizers, thickeners, non-reactive plasticizers, fillers, toughening agents (such as elastomers and rubbers) and chelators (see U.S. Pat. No. 6,391,993, incorporated herein by reference) may be included to modify the physical property and/or cure profile of the formulation and/or the strength or temperature resistance of the cured adhesive.

When used, the co-reactant, reactive diluent, plasticizer, mono- or poly-hydroxyalkanes, filler and/or toughening agent may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into anaerobic curable compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tetramethylbutyl hydroperoxide and combinations thereof.

Such peroxides are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. No. 4,287,350 (Rich) and U.S. Pat. No. 4,321,349 (Rich). Maleic acid is ordinarily added to APH-containing anaerobic cure inducing compositions.

Co-accelerators of free radical polymerization may also be used, chief among them being aromatic sulfimides, such as benzoic sulfimide (also known as saccharin) (see U.S. Pat. No. 3,218,305).

Stabilizers and inhibitors (such as phenols including hydroquinone and quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive cure accelerators may be used in amounts of about 0.1 to about 5 percent by weight, such as about 1 to about 2 percent by weight, based on the total weight of the composition. When used in combination with conventional accelerators (though at lower levels than such conventional accelerators), the inventive accelerators should be used in amounts of about 0.01 to about 5 percent by weight, such as about 0.02 to about 2 percent by weight, based on the total weight of the composition.

The present invention also provides methods of preparing and using the inventive anaerobically curable compositions, as well as reaction products of the compositions.

The compositions of the present invention may be prepared using conventional methods which are well known to those persons of skill in the art. For instance, the components of the inventive anaerobic adhesive and sealant compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

In addition, the invention provides a method of preparing an anaerobic curable composition, a step of which includes mixing together a (meth)acrylate component, and the anaerobic cure-inducing composition comprising the combination of peroxide and compound shown in structure I.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, compounds of structure I. That method involves providing an anaerobic curable composition comprising a (meth)acrylate component; providing an anaerobic cure-inducing composition comprising the compounds of, structure I; and exposing the anaerobic curable composition and the cure accelerator to conditions favorable to cure the composition.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

In view of the above description of the present invention, it is clear that a wide range of practical opportunities are provided. The following examples are illustrative purposes only, and are not to be construed so as to limit in any way the teaching herein.

Examples

Synthesis

N-Ethyl Acetate Tetrahydroquinoline

To a 1000 mL four-neck round bottom flask, equipped with a condenser, thermocouple, stir bar, magnetic stirrer, and a nitrogen inlet, is added tetrahydroquinoline (50 g, 0.38 mol), ethyl bromoacetate (75.2 g, 0.45 mol), diisopropylethylamine (58.2 g, 0.45 mol), and acetonitrile (500 mL) with stirring. The solution was heated to reflux. The reaction was stirred at reflux for four hours. The reaction mixture was added to 500 mL each of $H_2O$ and i-$Pr_2O$ in a 2000 mL separatory funnel. The aqueous layer was removed, and the organic layer was washed three times with 500 mL each of $H_2O$. The organic layer was separated, dried ($MgSO_4$), and filtered. Solvent was removed under reduced pressure. The residue was distilled under vacuum. Crude Yield=77.5 g (94%); B.P. (° C.)=130-133/2.0 Torr. Five fractions were collected, and fractions 2-5 were combined as pure product. Distilled Yield=75.4 g (92%); $^1$H NMR (CDCl$_3$) δδ 6.95-7.05 (m, 2, Ar—H), 6.6 (t, 1, Ar—H), 6.4 (d, 1, Ar—H), 4.2 (q, 2, O—CH$_2$), 4.0 (s, 2, N—CH$_2$—COO), 3.4 (t, 2, N—CH$_2$), 2.8 (t, 2, Ar—CH$_2$), 2.0 (m, 2, CH$_2$), 1.3 (t, 3, CH$_3$); $^{13}$C NMR (CDCl$_3$) 171, 145, 129, 127, 123, 117, 110, 61, 53, 51, 28, 22, 14; IR (neat) 2931, 1745, 1729, 1601, 1499, 1329, 1179, 1022, 971, 742 cm$^{-1}$.

N-Acetonitrile Tetrahydroquinoline

The same procedure as above was used with tetrahydroquinoline (75 g, 0.44 mol), bromoacetonitrile (81.2 g, 0.68 mol), diisopropylethylamine (87.3 g, 0.68 mol), and acetonitrile (500 mL). Crude Yield=100 g; B.P. (° C.)=134-135/2.0 Torr. Five fractions were collected, and fractions 2-5 were combined as pure product. Distilled Yield=81.2 g (84%); $^1$H NMR (CDCl$_3$) δδ 7.1 (t, 1, Ar—H), 7.0 (d, 1, Ar—H), 6.7 (t, 1, Ar—H), 6.6 (d, 1, Ar—H), 4.0 (s, 2, N—CH$_2$—CN), 3.3 (t, 2, N—CH$_2$), 2.8 (t, 2, Ar—CH$_2$), 2.0 (m, 2, CH$_2$); $^{13}$C NMR (CDCl$_3$) 143, 129, 127, 125, 119, 116, 112, 50, 40, 27, 22; IR (neat) 2932, 2238 (CN), 1603, 1496, 1328, 1240, 1194, 861, 742, 713 cm$^{-1}$. The product crystallized on standing at ambient temperature.

N-Ethyl Acetate Indoline

The same procedure as above was used with indoline (50 g, 0.42 mol), ethyl bromoacetate (83.5 g, 0.50 mol), diisopropylethylamine (64.5 g, 0.50 mol), and acetonitrile (500 mL). Crude Yield=91.1 g; B.P. (° C.)=120-123/2.0 Torr. Five fractions were collected, and fractions 2-5 were combined as pure product. Distilled Yield=80.3 g (93%); $^1$H NMR (CDCl$_3$) δδ 7.0-7.1 (m, 2, Ar—H), 6.7 (t, 1, Ar—H), 6.4 (d, 1, Ar—H), 4.2 (q, 2, O—CH$_2$), 3.9 (s, 2, N—CH$_2$—COO), 3.5 (t, 2, N—CH$_2$), 3.0 (t, 2, Ar—CH$_2$), 1.3 (t, 3, CH$_3$); $^{13}$C NMR (CDCl$_3$) 170, 151, 129, 127, 124, 118, 107, 61, 54, 50, 28, 14; IR (neat) 2980, 1744, 1731, 1607, 1489, 1251, 1180, 1020, 742, 709 cm$^{-1}$.

N-Acetonitrile Indoline

The same procedure was used with indoline (50 g, 0.42 mol), bromoacetonitrile (60.0 g, 0.50 mol), diisopropylethylamine (64.5 g, 0.50 mol), and acetonitrile (500 mL). Crude Yield=69.9 g; B.P. (° C.)=125-130/2.0 Torr. Five fractions were collected, and fractions 3-5 were combined as pure product. Distilled Yield=55.5 g (83%); $^1$H NMR (CDCl$_3$) δδ 7.1 (m, 2, Ar—H), 6.8 (t, 1, Ar—H), 6.6 (d, 1, Ar—H), 4.0 (s, 2, N—CH$_2$—CN), 3.4 (t, 2, N—CH$_2$), 2.8 (t, 2, Ar—CH$_2$); $^{13}$C NMR (CDCl$_3$) 149, 130, 127, 124, 115, 108, 53, 37, 28; IR (neat) 2848, 2238 (CN), 1607, 1486, 1309, 1242, 1149, 870, 750, 719 cm$^{-1}$. The product crystallized on standing at ambient temperature.

N-Ethyl Acetate-N-Methyl-Aniline

The same procedure as above was used with N-methyl aniline (53.5 g, 0.50 mol), ethyl bromoacetate (100.2 g, 0.60 mol), diisopropylethylamine (77.4 g, 0.60 mol), and acetonitrile (500 mL). Crude Yield=102.7 g; B.P. (° C.)=99-101/1.0 Torr. Five fractions were collected, and fractions 3-5 were combined as pure product. Distilled Yield=76.9 g (80%); $^1$H NMR (CDCl$_3$) δδ 7.2 (t, 2, Ar—H), 6.8 (t, 1, Ar—H), 6.7 (d, 2, Ar—H), 4.2 (q, 2, O—CH$_2$), 4.0 (s, 2, N—CH$_2$—COO), 3.0 (s, 3, N—CH$_3$), 1.3 (t, 3, CH$_3$); $^{13}$C NMR (CDCl$_3$) 170, 149, 129, 112, 107, 61, 54, 39, 14; IR (neat) 2981, 1745, 1729, 1600, 1505, 1366, 1184, 1117, 1027, 945, 747, 689 cm$^{-1}$.

N-Acetonitrile-N-Methyl-Aniline

The same procedure as above was used with N-methyl aniline (30.2 g, 0.28 mol), bromoacetonitrile (40.7 g, 0.34 mol), diisopropylethylamine (43.7 g, 0.34 mol), and acetonitrile (500 mL). Crude Yield=58.1 g; B.P. (° C.)=98-99/2.0 Torr. Five fractions were collected, and fractions 3-5 were combined as pure product. Distilled Yield=28.8 g (57%): $^1$H NMR (CDCl$_3$) δδ 7.3 (t, 2, Ar—H), 6.9 (t, 1, Ar—H), 6.8 (d, 2, Ar—H), 4.1 (s, 2, N—CH$_2$—COO), 3.0 (s, 3, N—CH$_3$); $^{13}$C NMR (CDCl$_3$) 147, 129, 120, 115, 114, 41, 39; IR (neat) 2819, 2238 (CN), 1599, 1500, 1335, 1245, 1117, 998, 924, 753, 690 cm$^{-1}$.

N-Nitrobenzyl Tetrahydroquinoline

To a 1000 mL four-neck round bottom flask, equipped with a condenser, thermocouple, stir bar, magnetic stirrer, and a nitrogen inlet, is added tetrahydroquinoline (25 g, 0.19 mol), nitrobenzyl bromide (40.6 g, 0.19 mol), diisopropyl-ethylamine (27.1 g, 0.21 mol), and acetonitrile (500 mL) with stirring. The solution was heated to reflux. The reaction was stirred at reflux for four hours. The reaction mixture was added to 500 mL each of $H_2O$ and EtOAc in a 2000 mL separatory funnel. The aqueous layer was removed, and the organic layer was washed three times with 500 mL each of $H_2O$. The organic layer was separated, dried ($MgSO_4$), and filtered. Solvent was removed under reduced pressure. The product was isolated as a crystalline, orange solid. Yield=77.5 g (94%); M.P.=101° C.: $^1$H NMR ($CDCl_3$) δ 8.2 (d, 2, Ar—H), 7.4 (d, 2, Ar—H), 6.95-7.05 (m, 2, Ar—H), 6.6 (t, 1, Ar—H), 6.3 (d, 1, Ar—H), 4.5 (s, 2, N—$CH_2$—Ar), 3.4 (t, 2, N—$CH_2$), 2.8 (t, 2, Ar—$CH_2$), 2.0 (m, 2, $CH_2$): $^{13}$C NMR ($CDCl_3$) 147.2, 147.0, 145, 129, 127, 124, 122, 117, 111, 55, 50, 28, 22; IR (neat) 2944, 1597, 1505, 1339, 1329, 1107, 950, 857, 732 cm$^{-1}$.

N-Cyanobenzyl Tetrahydroquinoline

The same procedure as above was used with tetrahydroquinoline (18.3 g, 137 mmol), 4-cyanobenzyl bromide (25.0 g, 137 mmol), diisopropyl-ethylamine (18.1 g, 140 mmol), and acetonitrile (500 mL). Yield=32.4 g (quant.); M.P.=ca. 35° C.: $^1$H NMR ($CDCl_3$) 87.6 (Ar—H), 7.4 (d, 2, Ar—H), 7.0 (m, 2, Ar—H), 6.6 (t, 1, Ar—H), 6.3 (d, 1, Ar—H), 4.5 (s, 2, N—$CH_2$—Ar), 3.4 (t, 2, N—$CH_2$), 2.8 (t, 2, Ar—$CH_2$), 2.0 (m, 2, $CH_2$): $^{13}$C NMR ($CDCl_3$) 145, 132, 129, 127, 122, 125, 119, 117, 116, 114, 111, 110, 55, 50, 27, 22; IR (neat) 2838, 2225, 1601, 1504, 1438, 1307, 1155, 973, 811, 743, 711 cm$^{-1}$. The product crystallized on standing at ambient temperature.

N-Nitrobenzyl Indoline

The same procedure as above was used with indoline (25.0 g, 210 mmol), nitrobenzyl bromide (45.4 g, 210 mmol), diisopropyl-ethylamine (29.7 g, 230 mmol), and acetonitrile (500 mL). Yield=50.5 g (95%); M.P.=99° C.: $^1$H NMR ($CDCl_3$) δ 8.2 (d, 2, Ar—H), 7.5 (d, 2, Ar—H), 7.0-7.1 (m, 2, Ar—H), 6.7 (t, 1, Ar—H), 6.4 (d, 1, Ar—H), 4.3 (s, 2, N—$CH_2$—Ar), 3.4 (t, 2, N—$CH_2$), 3.0 (t, 2, Ar—$CH_2$): $^{13}$C NMR ($CDCl_3$) 151, 147, 146, 130, 128, 127, 124, 123, 118, 107, 54, 53, 28; IR (neat) 2836, 1597, 1509, 1488, 1339, 1235, 1105, 1020, 845, 737, 712 cm$^{-1}$.

N-Cyanobenzyl Indoline

The same procedure as above was used with indoline (16.3 g, 137 mmol), cyanobenzyl bromide (25.0 g, 137 mmol), diisopropyl-ethylamine (18.1 g, 140 mmol), and acetonitrile (500 mL). Yield=30.1 g (quant.); M.P.=ca. 35° C.: $^1$H NMR ($CDCl_3$) δ 7.6 (d, 2, Ar—H), 7.4 (d, 2, Ar—H), 7.0-7.1 (m, 2, Ar—H), 6.7 (t, 1, Ar—H), 6.4 (d, 1, Ar—H), 4.3 (s, 2, N—$CH_2$—Ar), 3.3 (t, 2, N—$CH_2$), 3.0 (t, 2, Ar—$CH_2$): $^{13}$C NMR ($CDCl_3$) 152, 144, 132, 130, 128, 127, 124, 119, 118, 111, 107, 54, 53, 29; IR (neat) 2835, 2220, 1604, 1485, 1377, 1236, 1146, 1022, 823, 747, 718 cm$^{-1}$.

Preparation of Anaerobic Curable Compositions

The following components listed in the table below were used to make anaerobic curable compositions for evaluation:

| Materials | 1 (phr) | 2 (phr) |
| --- | --- | --- |
| PEGMA | 100 | 100 |
| Radical inhibitor solution | 0.42 | 0.42 |
| Chelator solution | 2.1 | 2.1 |
| Saccharin | 1.05 | 1.05 |
| Hydroperoxide | 0.9 | 0.9 |
| Acrylic acid | — | 5.0 |
| Aromatic amine curative | Equimolar amounts 1-2 | Equimolar amounts 1-2 |

Two base formulations were thus prepared, one based on polyethylene glycol dimethacrylate ("PEGMA") and the other based on PEGMA and acrylic acid. The remaining components make up the anaerobic cure system, with the accelerator varied as to identity as set forth below. The aromatic amine curative used as the accelerator was used in an equimolar amount; that is, within the range of 1-2 percent by weight.

Fifteen nut and bolt specimens of steel and stainless steel (having been degreased) were assembled for each formulation tested. For the break/prevail adhesion tests, the specimens were maintained at ambient temperature for 15 minutes, 1 hour, and 24 hours after assembly. The break and prevail torque strengths (measured in in.-lbs.) were then recorded after 15 minutes, 1 hour, and 24 hours at room temperature (25° C.) and 45-50% relative humidity, respectively. The break torque strengths (also measured in in.-lbs.) were then recorded after 15 minutes, 1 hour, and 24 hours at room temperature (25° C.) and 45-50% relative humidity, respectively.

Each of these formulations was also applied to fifteen replicates of steel pins and collars (having been degreased), and maintained at ambient temperature for 15 minutes, 1 hour, and 24 hours at room temperature (25° C.) and 45-50% relative humidity, respectively.

Break torque is the initial torque required to decrease or eliminate the axial load in a seated assembly. Prevail torque, after initial breakage of the bond, is measured at any point during 360° rotation of the nut. Prevail torque is normally determined at 180° rotation of the nut. Steel and stainless steel ⅜×16 nuts and bolts were degreased with 1,1,1-trichloroethylene, adhesive was applied to the bolt, and the nut was screwed onto the bolt.

The torque strengths were measured using a calibrated automatic torque analyzer. The data for the evaluations is set forth below in the tables and in the Figures.

Adhesive strength data for ethyl acetate tetrahydroquinoline (EtAc THQ), acetonitrile tetrahydroquinoline (AcCN THQ), ethyl acetate indoline (EtAc IND), and acetonitrile indoline (AcCN IND), along with DE-p-T/DM-o-T, indoline and THQ as controls, in Formulation 1 are captured in Tables 1-5 below and shown as bar charts in FIGS. 1-5.

In Table 1 below, the breakaway strength (measured in in.-lbs. after the noted time interval) on steel nut and bolt assemblies for Formulation 1 with the various accelerators is shown.

TABLE 1

|  | 15 min. (in · lbs.) | 1 hr. (in · lbs.) | 24 hrs. (in · lbs.) |
| --- | --- | --- | --- |
| DE-p-T/DM-o-T | 19 | 34 | 77 |
| THQ | 35 | 37 | 64 |
| Indoline | 14 | 67 | 49 |
| AcCN THQ | 0 | 28 | 57 |
| EtAc THQ | 12 | 33 | 72 |

TABLE 1-continued

|  | 15 min. (in · lbs.) | 1 hr. (in · lbs.) | 24 hrs. (in · lbs.) |
|---|---|---|---|
| AcCN IND | 24 | 43 | 80 |
| EtAc IND | 18 | 31 | 72 |

These data are shown graphically with reference to FIG. 1.

In Table 2 below, the prevail strength (measured in in.-lbs. after the noted time interval) on steel nut and bolt assemblies for Formulation 1 with the various accelerators is shown.

TABLE 2

|  | 15 min. (in · lbs.) | 1 hr. (in · lbs.) | 24 hrs. (in · lbs.) |
|---|---|---|---|
| DE-p-T/DM-o-T | 178 | 203 | 287 |
| THQ | 123 | 248 | 265 |
| Indoline | 235 | 293 | 345 |
| AcCN THQ | 0 | 154 | 243 |
| EtAc THQ | 150 | 203 | 359 |
| AcCN IND | 125 | 243 | 299 |
| EtAc IND | 135 | 215 | 326 |

Figure 2:
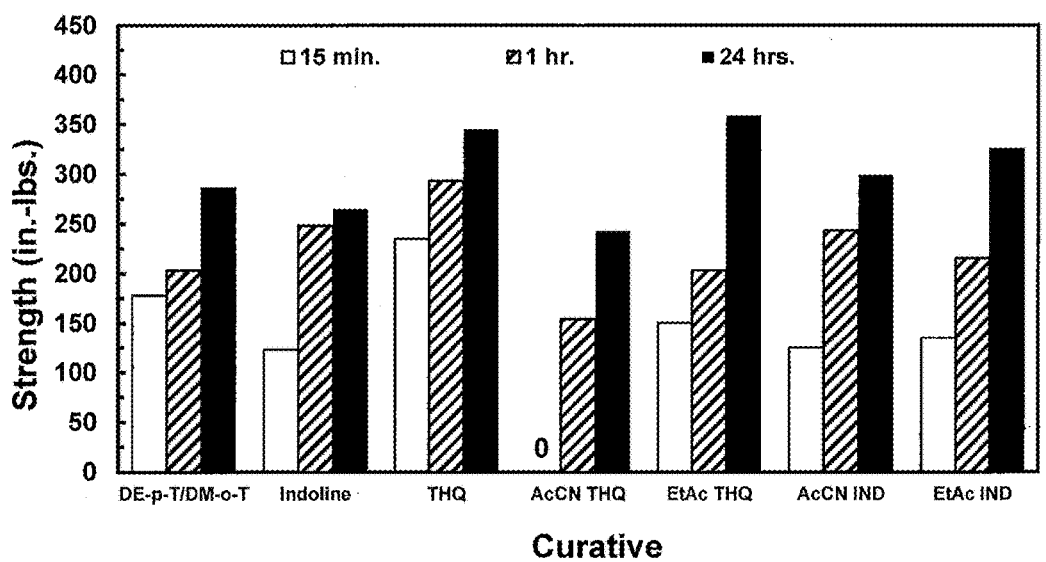
FIG. 2 depicts a plot of prevail strength vs. cure time of the anaerobic adhesive composition (Formulation 1), some of which using the inventive cure accelerators and others using conventional ones, on steel nuts and bolts.

These data are shown graphically with reference to FIG. 2.

In Table 3 below, the breakaway strength (measured in in.-lbs. after the noted time interval) on stainless steel nut and bolt assemblies for Formulation 1 with the various accelerators is shown.

TABLE 3

|  | 15 min. (in · lbs.) | 1 hr. (in · lbs.) | 24 hrs. (in · lbs.) |
|---|---|---|---|
| DE-p-T/DM-o-T | 0 | 14 | 13 |
| THQ | 14 | 11 | 11 |
| Indoline | 0 | 16 | 10 |
| AcCN THQ | 0 | 5 | 11 |
| EtAc THQ | 6 | 11 | 23 |
| AcCN IND | 6 | 8 | 10 |
| EtAc IND | 8 | 7 | 7 |

Figure 3:
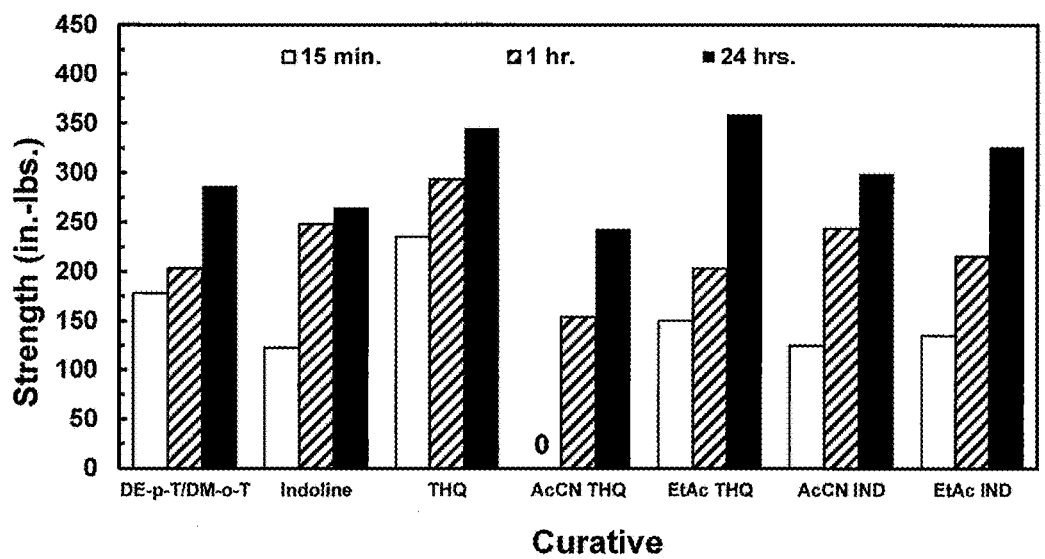
FIG. 3 depicts a plot of break strength vs. cure time of the anaerobic adhesive composition (Formulation 1), some of which using the inventive cure accelerators and others using conventional ones, on stainless steel nuts and bolts.

These data are shown graphically with reference to FIG. 3.

In Table 4 below, the prevail strength (measured in in.-lbs. after the noted time interval) on stainless steel nut and bolt assemblies for Formulation 1 with the various accelerators is shown.

TABLE 4

|  | 15 min. (in · lbs.) | 1 hr. (in · lbs.) | 24 hrs. (in · lbs.) |
|---|---|---|---|
| DE-p-T/DM-o-T | 0 | 74 | 134 |
| THQ | 37 | 184 | 238 |
| Indoline | 0 | 87 | 209 |
| AcCN THQ | 0 | 6 | 128 |
| EtAc THQ | 2 | 146 | 139 |
| AcCN IND | 2 | 122 | 177 |
| EtAc IND | 23 | 117 | 221 |

Figure 4:
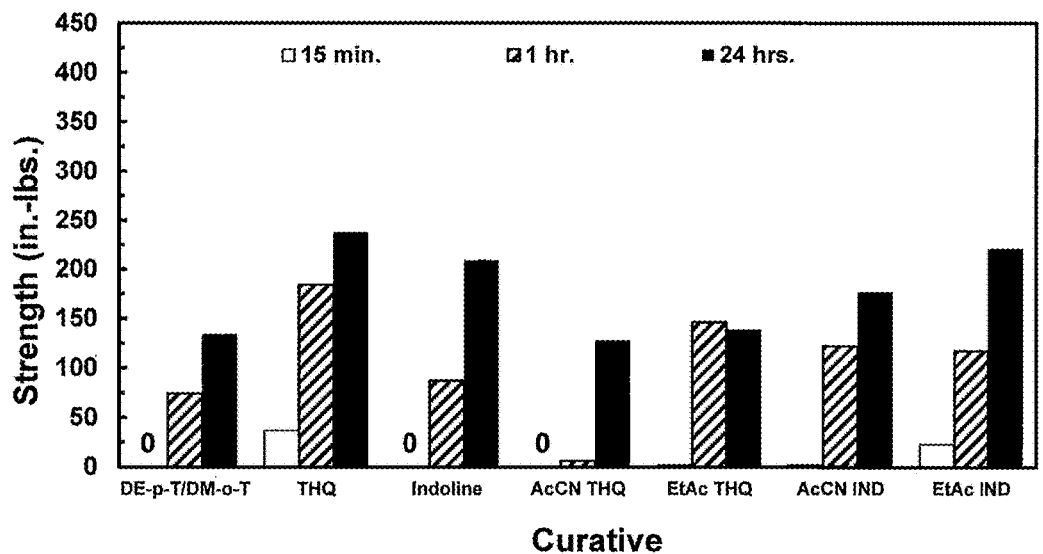
FIG. 4 depicts a plot of prevail strength vs. cure time of the anaerobic adhesive composition (Formulation 1), some of which using the inventive cure accelerators and others using conventional ones, on stainless steel nuts and bolts.

These data are shown graphically with reference to FIG. 4.

In Table 5 below, the tensile strength (measured in psi after the noted time interval) on steel pin and collar assemblies for Formulation 1 with the various accelerators is shown.

TABLE 5

|  | 15 min. (psi) | 60 min. (psi) | 24 hrs. (psi.) |
|---|---|---|---|
| DE-p-T/DM-o-T | 106 | 1152 | 1843 |
| THQ | 770 | 1232 | 1611 |
| Indoline | 49 | 1330 | 1629 |
| NB THQ | 0 | 278 | 1440 |
| CB THQ | 433 | 1346 | 1631 |
| NB IND | 338 | 1476 | 1411 |
| CB IND | 1413 | 1122 | 1693 |

Figure 5:
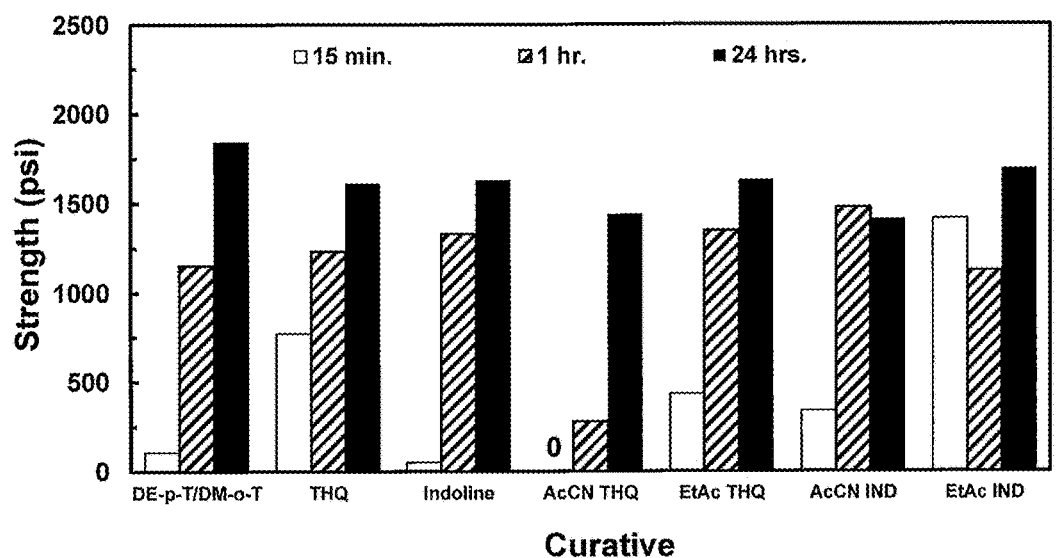
FIG. 5 depicts a plot of tensile strength vs. cure time of the anaerobic adhesive composition (Formulation 1), some of which using the inventive cure accelerators and others using conventional ones, on steel pins and collars.

These data are shown graphically with reference to FIG. 5.

Adhesive strength data for ethyl acetate tetrahydroquinoline (EtAc THQ), acetonitrile tetrahydroquinoline (AcCN THQ), ethyl acetate indoline (EtAc IND), and acetonitrile indoline (AcCN IND), along with DE-p-T/DM-o-T, indoline and THQ as controls, in Formulation 2 are captured in Tables 6-10 below and shown in bar charts in FIGS. 6-10.

In Table 6 below, the breakaway strength (measured in in.-lbs. after the noted time interval) on steel nut and bolt assemblies for Formulation 2 with the various accelerators is shown.

TABLE 6

|  | 15 min. (in. lbs.) | 1 hr. (in. lbs.) | 24 hrs. (in. lbs.) |
|---|---|---|---|
| DE-p-T/DM-o-T | 0 | 24 | 37 |
| THQ | 24 | 36 | 30 |
| Indoline | 10 | 37 | 23 |
| AcCN THQ | 0 | 28 | 35 |
| EtAc THQ | 7 | 19 | 45 |
| AcCN IND | 12 | 28 | 30 |
| EtAc IND | 13 | 24 | 37 |

Figure 6:
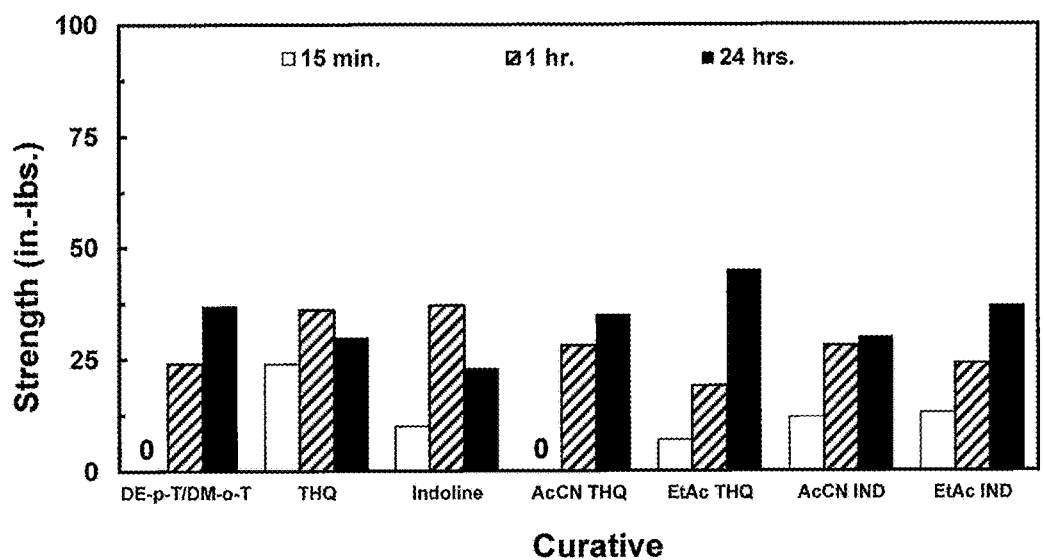
FIG. 6 depicts a plot of break strength vs. cure time of the anaerobic adhesive composition (Formulation 2), some of which using the inventive cure accelerators and others using conventional ones, on steel nuts and bolts.

These data are shown graphically with reference to FIG. 6.

In Table 7 below, the prevail strength (measured in in.-lbs. after the noted time interval) on steel nut and bolt assemblies for Formulation 2 with the various accelerators is shown.

TABLE 7

|  | 15 min. (in. lbs.) | 1 hr. (in. lbs.) | 24 hrs. (in. lbs.) |
|---|---|---|---|
| DE-p-T/DM-o-T | 0 | 159 | 199 |
| THQ | 216 | 268 | 266 |
| Indoline | 100 | 171 | 317 |
| AcCN THQ | 0 | 86 | 186 |
| EtAc THQ | 127 | 132 | 249 |
| AcCN IND | 147 | 229 | 265 |
| EtAc IND | 180 | 149 | 272 |

Figure 7:
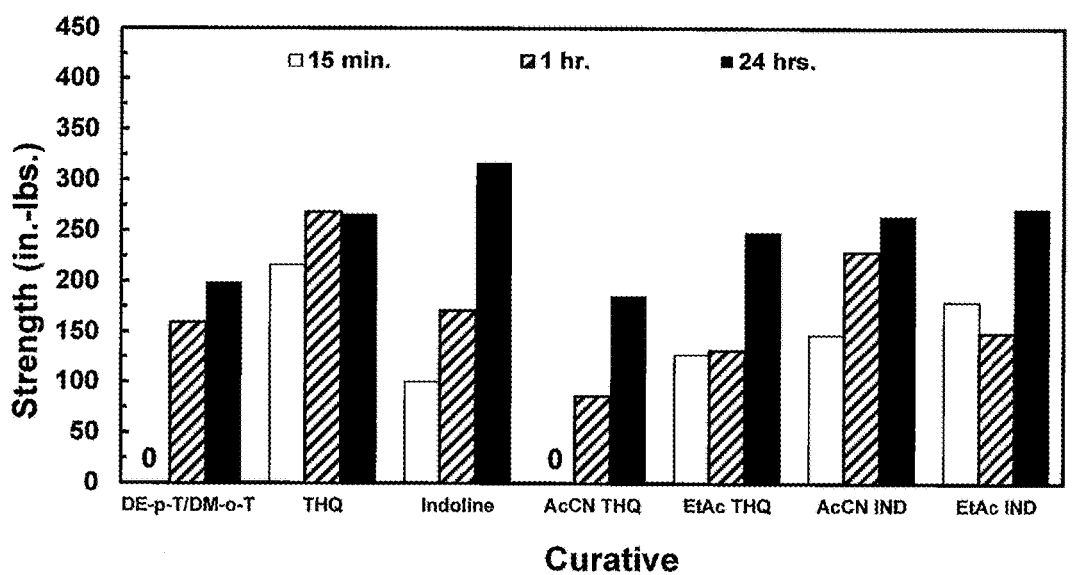
FIG. 7 depicts a plot of prevail strength vs. cure time of the anaerobic adhesive composition (Formulation 2), some of which using the inventive cure accelerators and others using conventional ones, on steel nuts and bolts.

These data are shown graphically with reference to FIG. 7.

In Table 8 below, the breakaway strength (measured in in.-lbs. after the noted time interval) on stainless steel nut and bolt assemblies for Formulation 2 with the various accelerators is shown.

TABLE 8

|  | 15 min. (in. lbs.) | 1 hr. (in. lbs.) | 24 hrs. (in. lbs.) |
|---|---|---|---|
| DE-p-T/DM-o-T | 0 | 8 | 11 |
| THQ | 11 | 13 | 17 |
| Indoline | 0 | 10 | 15 |
| AcCN THQ | 0 | 8 | 13 |
| EtAc THQ | 0 | 7 | 12 |

TABLE 8-continued

|  | 15 min. (in. lbs.) | 1 hr. (in. lbs.) | 24 hrs. (in. lbs.) |
| --- | --- | --- | --- |
| AcCN IND | 0 | 11 | 11 |
| EtAc IND | 13 | 15 | 20 |

Figure 8:
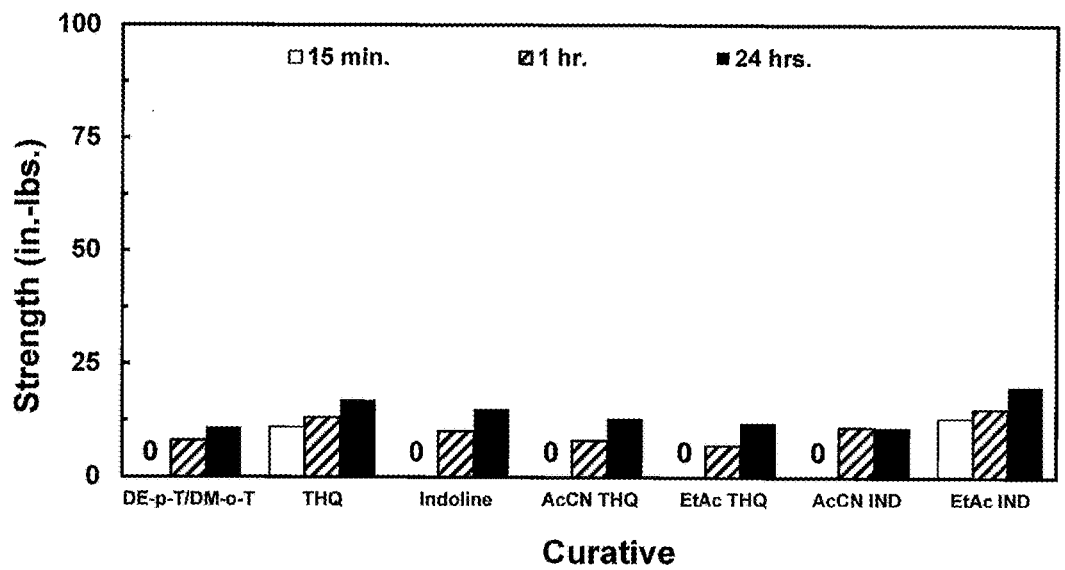
FIG. 8 depicts a plot of break strength vs. cure time of the anaerobic adhesive composition (Formulation 2), some of which using the inventive cure accelerators and others using conventional ones, on stainless steel nuts and bolts.

These data are shown graphically with reference to FIG. 8.

In Table 9 below, the prevail strength (measured in in.-lbs. after the noted time interval) on stainless steel nut and bolt assemblies for Formulation 2 with the various accelerators is shown.

TABLE 9

|  | 15 min. (in. lbs.) | 1 hr. (in. lbs.) | 24 hrs. (in. lbs.) |
| --- | --- | --- | --- |
| DE-p-T/DM-o-T | 0 | 42 | 125 |
| THQ | 109 | 202 | 190 |
| Indoline | 0 | 203 | 188 |
| AcCN THQ | 0 | 11 | 146 |
| EtAc THQ | 0 | 207 | 161 |
| AcCN IND | 0 | 139 | 172 |
| EtAc IND | 48 | 168 | 266 |

Figure 9:
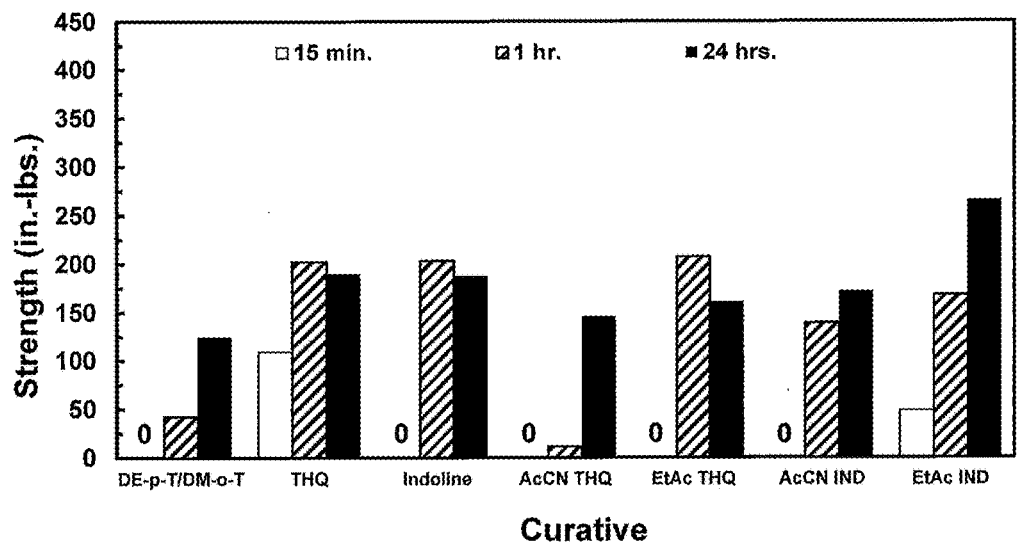
FIG. 9 depicts a plot of prevail strength vs. cure time of the anaerobic adhesive composition (Formulation 2), some of which using the inventive cure accelerators and others using conventional ones, on stainless steel nuts and bolts.

These data are shown graphically with reference to FIG. 9.

In Table 10 below, the tensile strength (measured in psi after the noted time interval) on steel nut and bolt assemblies for Formulation 2 with the various accelerators is shown.

TABLE 10

|  | 15 min. (psi) | 60 min. (psi) | 24 hrs. (psi.) |
| --- | --- | --- | --- |
| DE-p-T/DM-o-T | 0 | 383 | 1940 |
| THQ | 385 | 1745 | 2065 |
| Indoline | 64 | 1715 | 1867 |
| NB THQ | 0 | 165 | 1495 |
| CB THQ | 614 | 2012 | 1987 |
| NB IND | 211 | 1487 | 2135 |
| CB IND | 634 | 1582 | 1836 |

Figure 10:
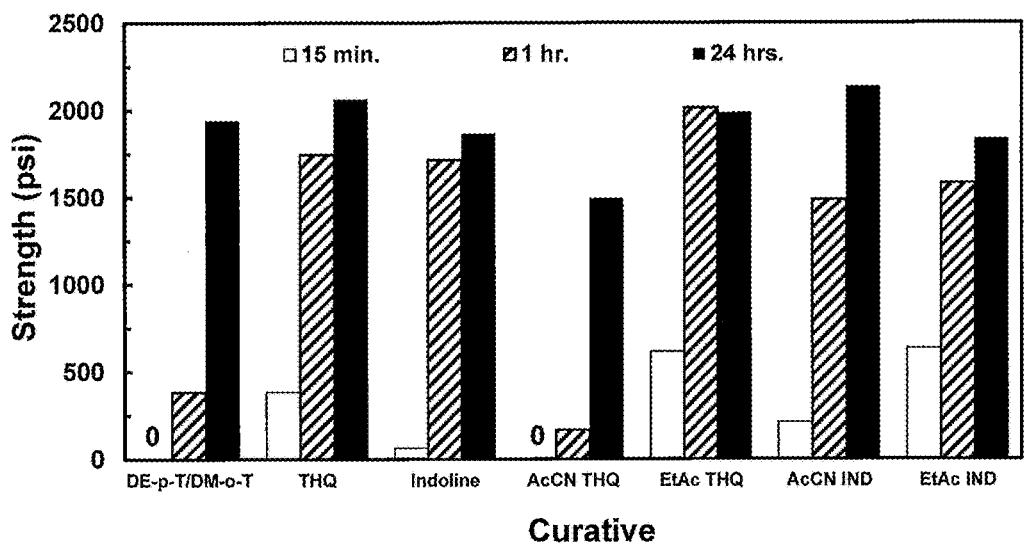
FIG. 10 depicts a plot of tensile strength vs. cure time of the anaerobic adhesive composition (Formulation 2), some of which using the inventive cure accelerators and others using conventional ones, on steel pins and collars.

These data are shown graphically with reference to FIG. 10.

Adhesive strength data for nitrobenzyl tetrahydroquinoline (NB THQ), cyanobenzyl tetrahydroquinoline (CB THQ), nitrobenzyl indoline (NB IND), and cyanobenzyl indoline (CB IND), along with DE-p-T/DM-o-T, indoline and THQ as controls, in Formulation 1 are captured in Tables 11-15 below and shown as bar charts in FIGS. 11-15.

In Table 11 below, the breakaway strength (measured in in.-lbs. after the noted time interval) on steel nut and bolt assemblies for Formulation 1 with the various accelerators is shown.

TABLE 11

|  | 15 min. (in. lbs.) | 60 min. (in. lbs.) | 24 hrs. (in. lbs.) |
| --- | --- | --- | --- |
| DE-p-T/DM-o-T | 19 | 34 | 77 |
| THQ | 35 | 37 | 64 |
| Indoline | 14 | 67 | 49 |
| NB THQ | 5 | 21 | 55 |
| CB THQ | 13 | 32 | 36 |
| NB IND | 11 | 26 | 34 |
| CB IND | 19 | 25 | 42 |

Figure 11:
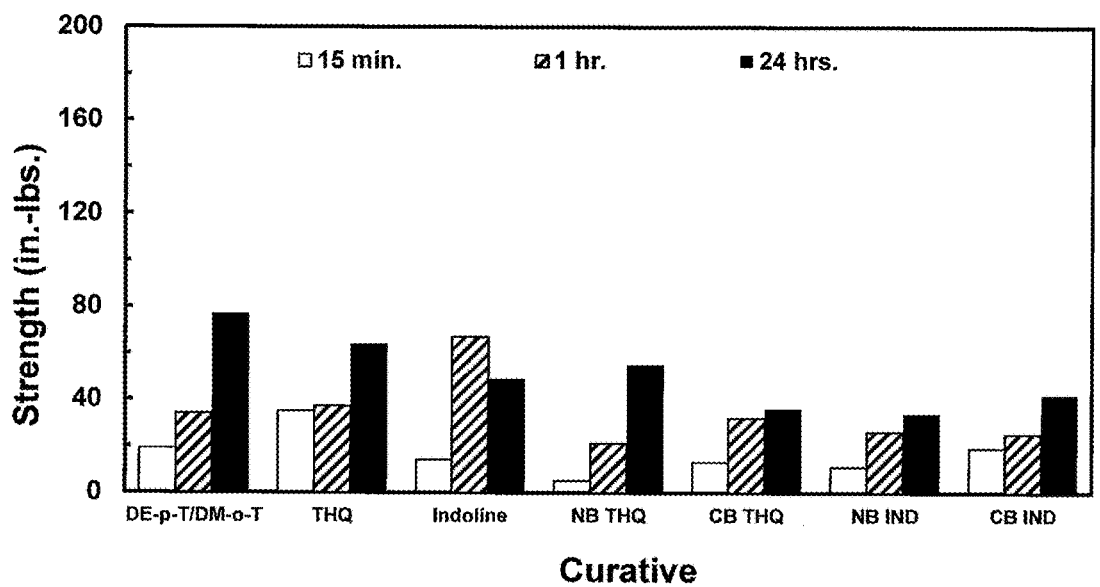
FIG. 11 depicts a plot of break strength vs. cure time of the anaerobic adhesive composition (Formulation 1), some of which using the inventive cure accelerators and others using conventional ones, on steel nuts and bolts.

These data are shown graphically with reference to FIG. 11.

In Table 12 below, the prevail strength (measured in in.-lbs. after the noted time interval) on steel nut and bolt assemblies for Formulation 1 with the various accelerators is shown.

TABLE 12

|  | 15 min. (in. lbs.) | 60 min. (in. lbs.) | 24 hrs. (in. lbs.) |
| --- | --- | --- | --- |
| DE-p-T/DM-o-T | 178 | 203 | 287 |
| THQ | 235 | 293 | 345 |
| Indoline | 123 | 248 | 265 |
| NB THQ | 3 | 148 | 210 |
| CB THQ | 15 | 124 | 151 |
| NB IND | 8 | 108 | 169 |
| CB IND | 83 | 132 | 184 |

Figure 12:
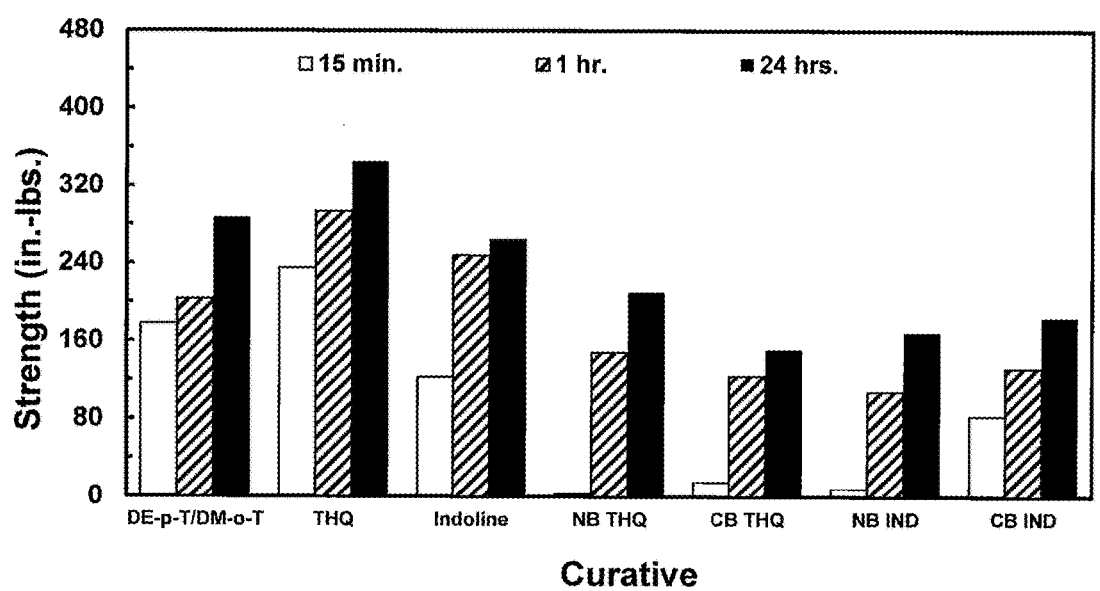
FIG. 12 depicts a plot of prevail strength vs. cure time of the anaerobic adhesive composition (Formulation 1), some of which using the inventive cure accelerators and others using conventional ones, on steel nuts and bolts.

These data are shown graphically with reference to FIG. 12.

In Table 13 below, the breakaway strength (measured in in.-lbs. after the noted time interval) on stainless steel nut and bolt assemblies for Formulation 1 with the various accelerators is shown.

TABLE 13

|  | 15 min. (in. lbs.) | 60 min. (in. lbs.) | 24 hrs. (in. lbs.) |
| --- | --- | --- | --- |
| DE-p-T/DM-o-T | 0 | 14 | 13 |
| THQ | 14 | 11 | 11 |
| Indoline | 0 | 16 | 10 |
| NB THQ | 9 | 10 | 13 |
| CB THQ | 19 | 13 | 15 |
| NB IND | 7 | 8 | 37 |
| CB IND | 10 | 15 | 13 |

Figure 13:
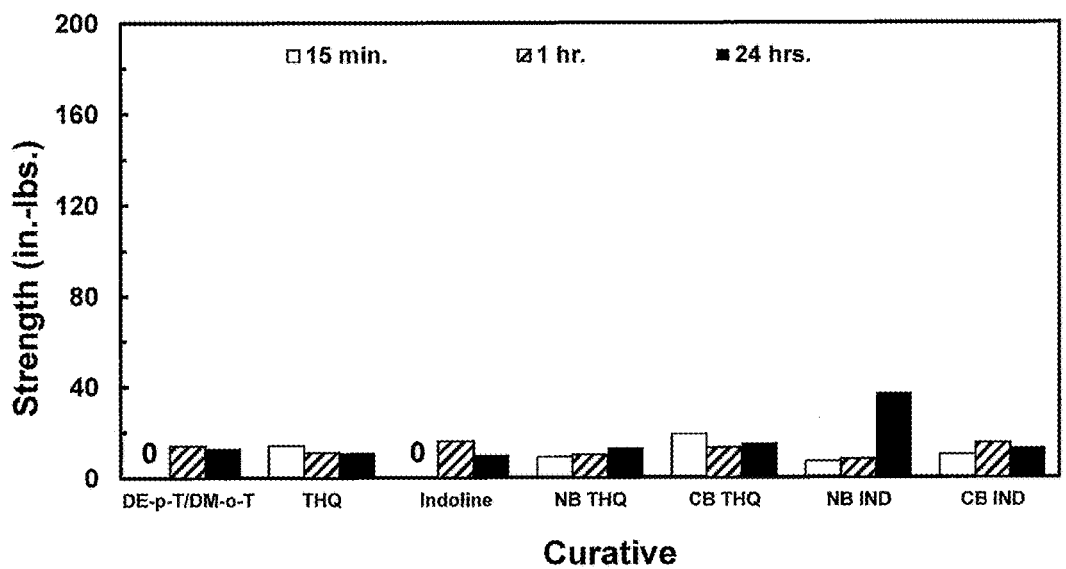
FIG. 13 depicts a plot of break strength vs. cure time of the anaerobic adhesive composition (Formulation 1), some of which using the inventive cure accelerators and others using conventional ones, on stainless steel nuts and bolts.

These data are shown graphically with reference to FIG. 13.

In Table 14 below, the prevail strength (measured in in.-lbs. after the noted time interval) on stainless steel nut and bolt assemblies for Formulation 1 with the various accelerators is shown.

TABLE 14

|  | 15 min. (in. lbs.) | 60 min. (in. lbs.) | 24 hrs. (in. lbs.) |
| --- | --- | --- | --- |
| DE-p-T/DM-o-T | 0 | 74 | 134 |
| THQ | 37 | 184 | 238 |
| Indoline | 0 | 87 | 209 |
| NB THQ | 12 | 107 | 220 |
| CB THQ | 93 | 162 | 172 |
| NB IND | 47 | 154 | 220 |
| CB IND | 124 | 203 | 196 |

Figure 14:
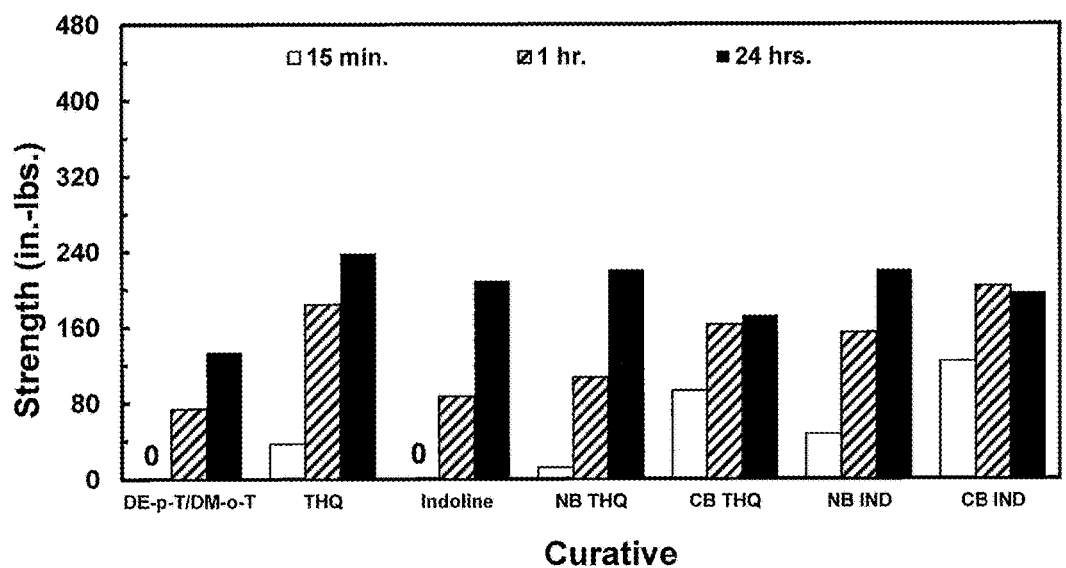
FIG. 14 depicts a plot of prevail strength vs. cure time of the anaerobic adhesive composition (Formulation 1), some of which using the inventive cure accelerators and others using conventional ones, on stainless steel nuts and bolts.

These data are shown graphically with reference to FIG. 14.

In Table 15 below, the tensile strength (measured in psi after the noted time interval) on steel pin and collar assemblies for Formulation 1 with the various accelerators is shown.

TABLE 15

|  | 15 min. (psi) | 60 min. (psi) | 24 hrs. (psi.) |
| --- | --- | --- | --- |
| DE-p-T/DM-o-T | 106 | 1152 | 1843 |
| THQ | 770 | 1232 | 1611 |
| Indoline | 49 | 1330 | 1629 |
| NB THQ | 992 | 1137 | 1550 |
| CB THQ | 705 | 1464 | 1788 |
| NB IND | 879 | 1330 | 1489 |
| CB IND | 1159 | 1271 | 1551 |

These data are shown graphically with reference to FIG. 15.

Adhesive strength data for nitrobenzyl tetrahydroquinoline (NB THQ), cyanobenzyl tetrahydroquinoline (CB THQ), nitrobenzyl indoline (NB IND), cyanobenzyl indoline (CB IND), along with DE-p-T/DM-o-T, indoline and THQ as controls, in Formulation 2 are captured in Tables 16-20 below and shown in bar charts in FIGS. 16-20.

In Table 16 below, the breakaway strength (measured in in.-lbs. after the noted time interval) on steel nut and bolt assemblies for Formulation 2 with the various accelerators is shown.

TABLE 16

|  | 15 min. (in. lbs.) | 60 min. (in. lbs.) | 24 hrs. (in. lbs.) |
| --- | --- | --- | --- |
| DE-p-T/DM-o-T | 0 | 24 | 37 |
| THQ | 24 | 36 | 30 |
| Indoline | 10 | 37 | 23 |
| NB THQ | 6 | 30 | 89 |
| CB THQ | 20 | 31 | 62 |
| NB IND | 19 | 29 | 55 |
| CB IND | 20 | 24 | 97 |

These data are shown graphically with reference to FIG. 16.

In Table 17 below, the prevail strength (measured in in.-lbs. after the noted time interval) on steel nut and bolt assemblies for Formulation 2 with the various accelerators is shown.

TABLE 17

|  | 15 min. (in. lbs.) | 60 min. (in. lbs.) | 24 hrs. (in. lbs.) |
| --- | --- | --- | --- |
| DE-p-T/DM-o-T | 0 | 159 | 199 |
| THQ | 216 | 268 | 266 |
| Indoline | 100 | 171 | 317 |
| NB THQ | 6 | 171 | 174 |
| CB THQ | 15 | 67 | 223 |
| NB IND | 30 | 152 | 237 |
| CB IND | 97 | 159 | 193 |

Figure 17:
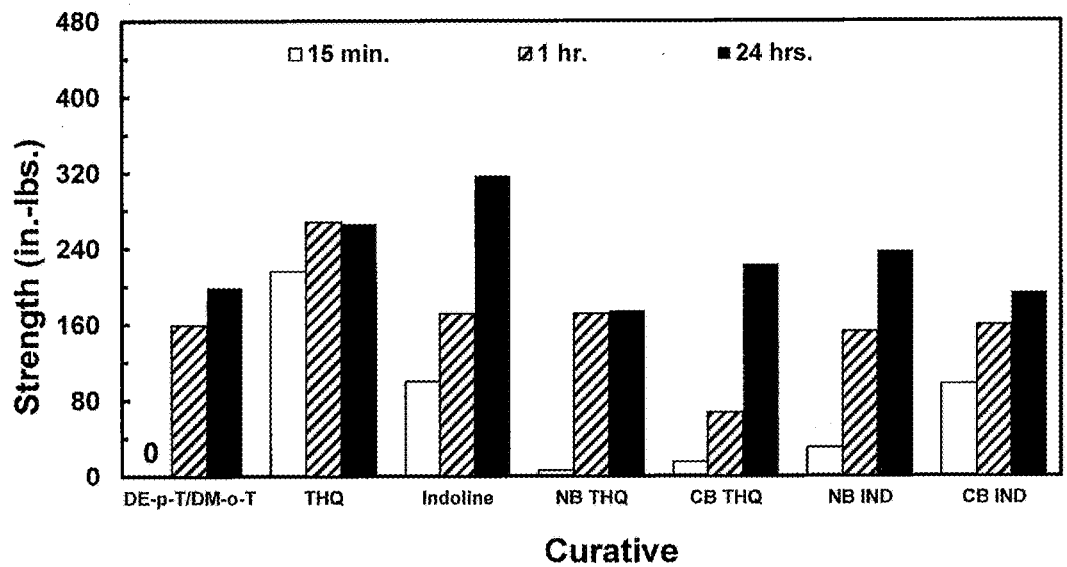
FIG. 17 depicts a plot of prevail strength vs. cure time of the anaerobic adhesive composition (Formulation 2), some of which using the inventive cure accelerators and others using conventional ones, on steel nuts and bolts.

These data are shown graphically with reference to FIG. 17.

In Table 18 below, the breakaway strength (measured in in.-lbs. after the noted time interval) on stainless steel nut and bolt assemblies for Formulation 2 with the various accelerators is shown.

TABLE 18

|  | 15 min. (in. lbs.) | 60 min. (in. lbs.) | 24 hrs. (in. lbs.) |
| --- | --- | --- | --- |
| DE-p-T/DM-o-T | 0 | 8 | 11 |

TABLE 18-continued

|  | 15 min. (in. lbs.) | 60 min. (in. lbs.) | 24 hrs. (in. lbs.) |
| --- | --- | --- | --- |
| THQ | 11 | 13 | 17 |
| Indoine | 0 | 10 | 15 |
| NB THQ | 8 | 8 | 13 |
| CB THQ | 12 | 13 | 11 |
| NB IND | 18 | 11 | 14 |
| CB IND | 16 | 10 | 11 |

Figure 18:
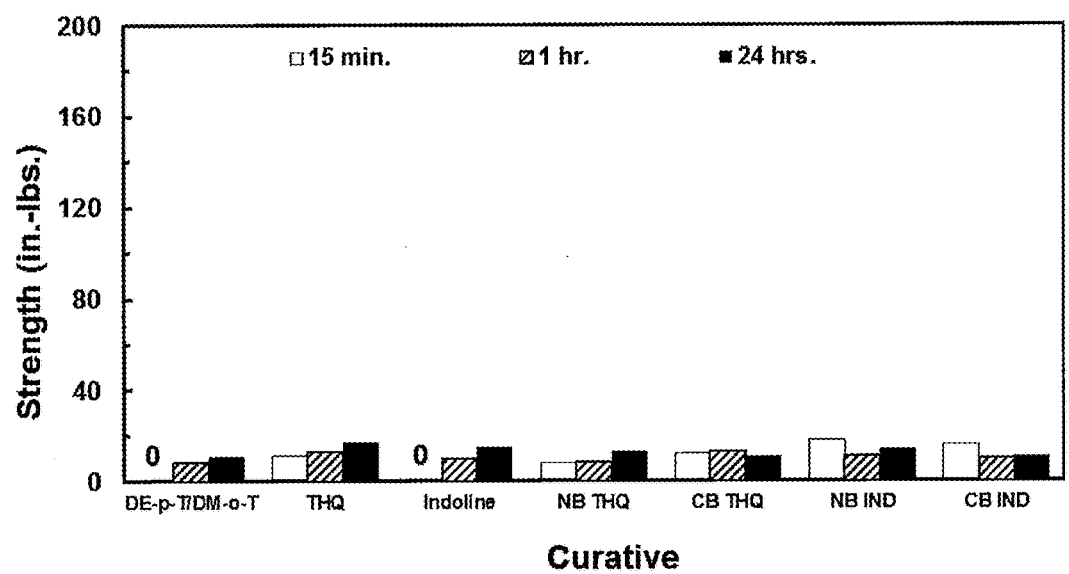
FIG. 18 depicts a plot of break strength vs. cure time of the anaerobic adhesive composition (Formulation 2), some of which using the inventive cure accelerators and others using conventional ones, on stainless steel nuts and bolts.

These data are shown graphically with reference to FIG. 18.

In Table 19 below, the prevail strength (measured in in.-lbs. after the noted time interval) on stainless steel nut and bolt assemblies for Formulation 2 with the various accelerators is shown.

TABLE 19

|  | 15 min. (in. lbs.) | 60 min. (in. lbs.) | 24 hrs. (in. lbs.) |
| --- | --- | --- | --- |
| DE-p-T/DM-o-T | 0 | 42 | 125 |
| THQ | 109 | 202 | 190 |
| Indoline | 0 | 203 | 188 |
| NB THQ | 8 | 76 | 211 |
| CB THQ | 36 | 138 | 166 |
| NB IND | 71 | 156 | 243 |
| CB IND | 72 | 152 | 198 |

Figure 19:
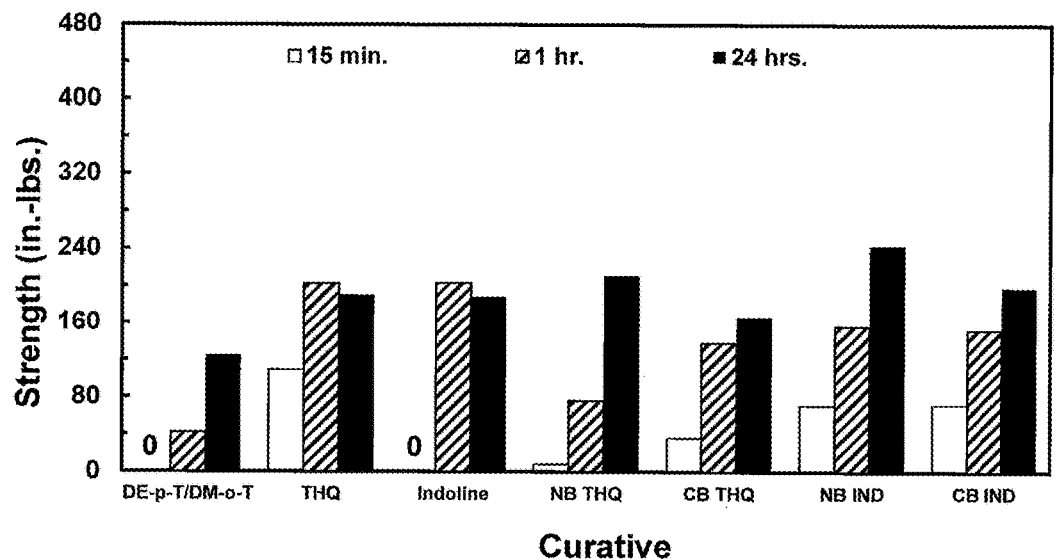
FIG. 19 depicts a plot of prevail strength vs. cure time of the anaerobic adhesive composition (Formulation 2), some of which using the inventive cure accelerators and others using conventional ones, on stainless steel nuts and bolts.

These data are shown graphically with reference to FIG. 19.

In Table 20 below, the tensile strength (measured in psi after the noted time interval) on steel nut and bolt assemblies for Formulation 2 with the various accelerators is shown.

TABLE 20

|  | 15 min. (psi) | 60 min. (psi) | 24 hrs. (psi.) |
| --- | --- | --- | --- |
| DE-p-T/DM-o-T | 0 | 383 | 1940 |
| THQ | 385 | 1745 | 2065 |
| Indoline | 64 | 1715 | 1867 |
| NB THQ | 287 | 1463 | 1922 |
| CB THQ | 1409 | 1770 | 2020 |
| NB IND | 1163 | 1402 | 2039 |
| CB IND | 1489 | 1916 | 1070 |

Figure 20:
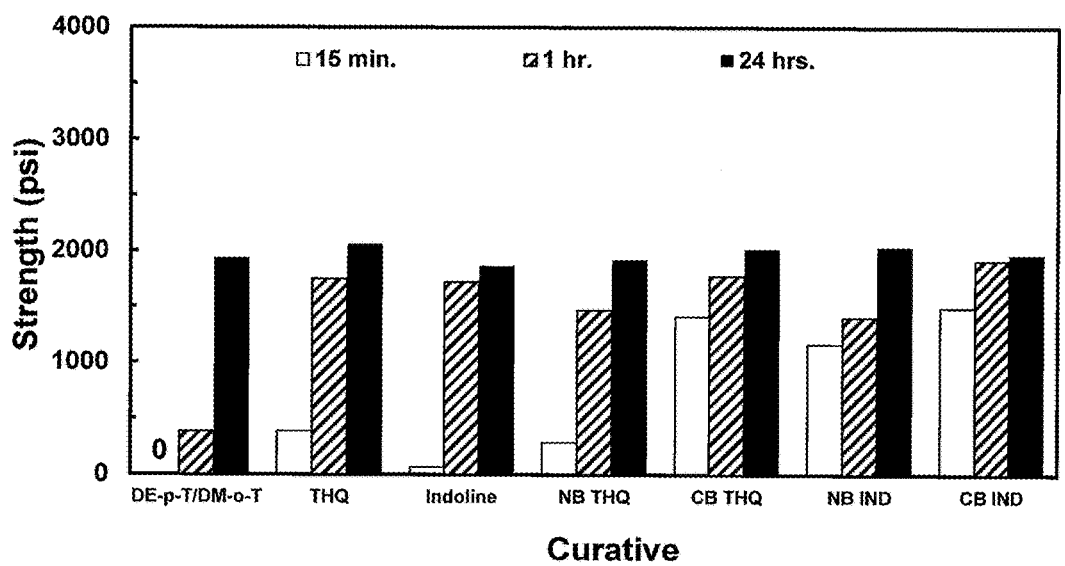
FIG. 20 depicts a plot of tensile strength vs. cure time of the anaerobic adhesive composition (Formulation 2), some of which using the inventive cure accelerators and others using conventional ones, on steel pins and collars.

These data are shown graphically with reference to FIG. 20.

This data indicates that formulations in accordance with this invention exhibited acceptable break and prevail properties at room temperature, and in some instances somewhat superior performance when compared to anaerobic curable compositions prepared with conventional accelerators having been applied and cured on the steel or stainless steel substrates. The lower odor exhibited by the inventive formulations coupled with expected reduced toxicity of the constituents may lead to less rigorous regulatory requirements and as a result may prove useful in some commercial applications and environments, and is another benefit to these compounds as cure accelerators in anaerobic curable compositions.

What is claimed is:
1. An anaerobic curable composition comprising
(a) a (meth)acrylate component;
(b) an anaerobic cure-inducing composition; and
(c) a compound selected from one or more of

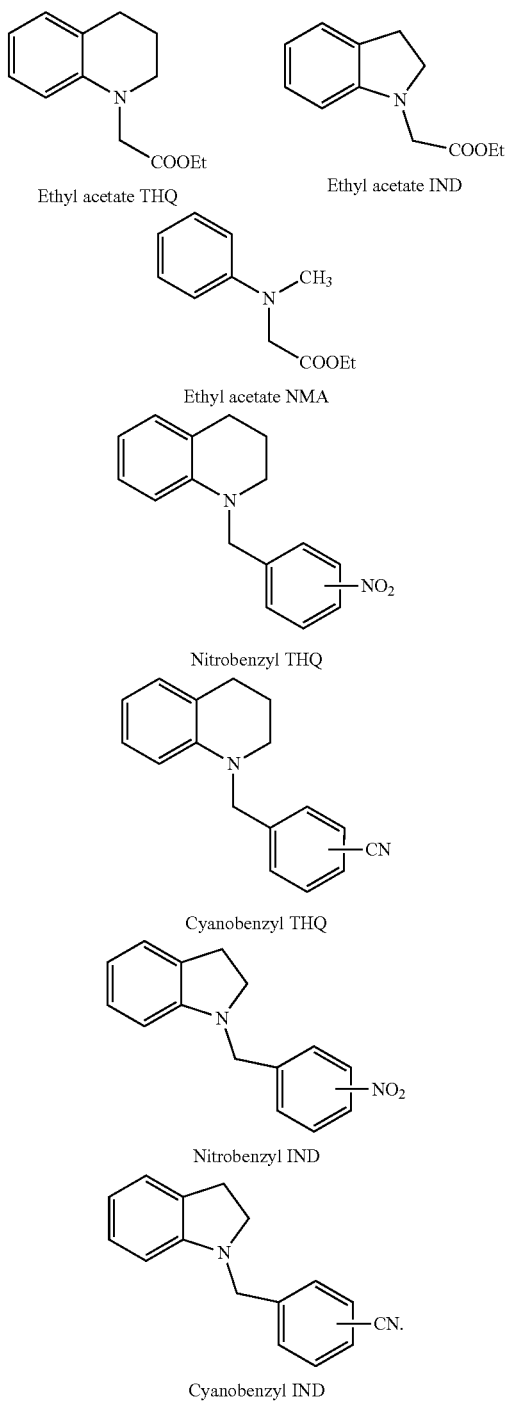

Ethyl acetate THQ

Ethyl acetate IND

Ethyl acetate NMA

Nitrobenzyl THQ

Cyanobenzyl THQ

Nitrobenzyl IND

Cyanobenzyl IND

2. The composition according to claim 1, wherein the anaerobic cure-inducing composition comprises a hydroperoxide selected from the group consisting of cumene hydroperoxide, para-menthane hydroperoxide, t-butyl hydroperoxide, t-butyl perbenzoate, benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tertramethylbutyl hydroperoxide and combinations thereof.

3. The composition according to claim 1, further comprising at least one co-accelerator.

4. The composition according to claim 3, wherein the co-accelerator is selected from the group consisting of amines, amine oxides, sulfimides, metals and sources thereof, acids, and mixtures thereof.

5. The composition according to claim 3, wherein the co-accelerator is selected from the group consisting of triazines, ethanolamine, diethanolamine, triethanolamine, N,N-dimethyl aniline, cyclohexyl amine, triethyl amine, butyl amine, saccharin, N,N-diethyl-p-toluidine, N,N-dimethyl-o-toluidine, and acetyl phenylhydrazine with maleic acid, and mixtures thereof.

6. The composition according to claim 1, further comprising at least one stabilizer.

7. The composition according to claim 6, wherein the stabilizer is selected from the group consisting of benzoquinone, naphthoquinone, anthraquinone, hydroquinone, methoxyhydroquinone, butylated hydroxy toluene, ethylene diamine tetraacetic acid or a salt thereof, and mixtures thereof.

8. A method of using as a cure accelerator for anaerobic curable compositions a compound shown in structure I:

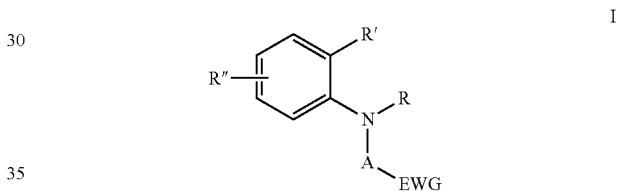

I wherein A is CH$_2$ or benzyl, R is C$_{1-10}$ alkyl, R' is H or C$_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is an electron withdrawing group, comprising the steps of:

(a) providing an anaerobic curable composition comprising a (meth)acrylate component and an anaerobic cure-inducing composition;

(b) providing as a cure accelerator for the anaerobic curable composition a compound shown in structure I:

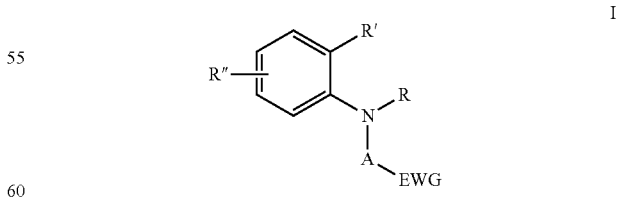

I wherein A is CH$_2$ or benzyl, R is C$_{1-10}$ alkyl, R' is H or C$_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is an electron withdrawing group; and
(c) exposing the anaerobic curable composition and the cure accelerator to conditions favorable to cure the composition.

9. A method of making a compound shown in structure I:

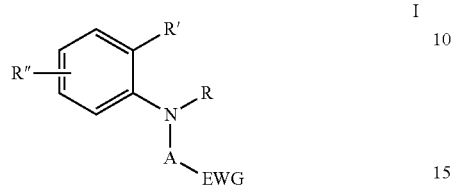

wherein A is $CH_2$ or $CH_2$phenyl (benzyl), R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is an electron withdrawing group, for accelerating cure of anaerobic curable compositions comprising, reacting:

(a)

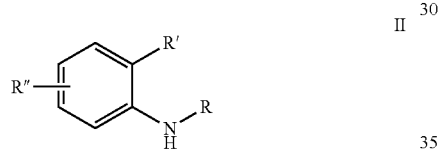

wherein R, R', and R" are as described above; and
(b) in the presence of a base, and an electron withdrawing group-containing methylene halide, an electron withdrawing group-containing tosylate or an electron withdrawing group-containing mesylate, wherein the electron withdrawing group is a member selected from the group consisting of esters, nitobenzyl and cyanobenzyl.

10. Compounds shown in structure I

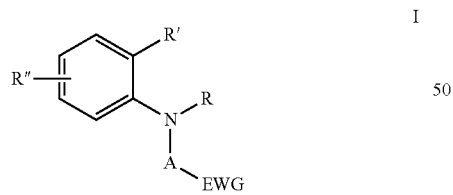

wherein A is $CH_2$ or benzyl, R is $C_{1-10}$ alkyl, R' is H or $C_{1-10}$ alkyl, or R and R' taken together may form a four to seven membered ring fused to the benzene ring, R" is optional, but when R" is present, R" is halogen, alkyl, alkenyl, cycloalkyl, hydroxyalkyl, hydroxyalkenyl, alkoxy, amino, alkylene- or alkenylene-ether, alkylene (meth)acrylate, carbonyl, carboxyl, nitroso, sulfonate, hydroxyl or haloalkyl, and EWG is an electron withdrawing group selected from the group consisting of esters, nitrobenzyl and cyanobenzyl.

11. Compounds selected from one or more of

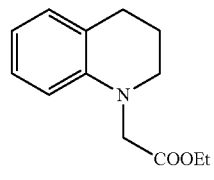
Ethyl acetate THQ

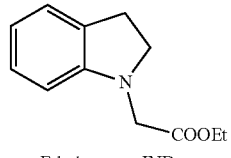
Ethyl acetate IND

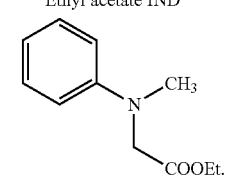
Ethyl acetate NMA

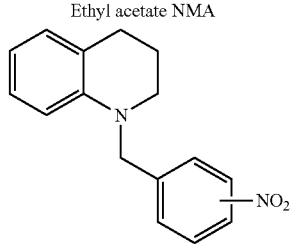
Nitrobenzyl THQ

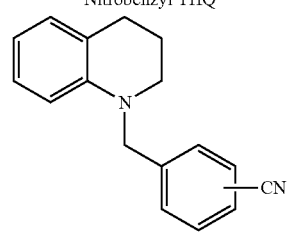
Cyanobenzyl THQ

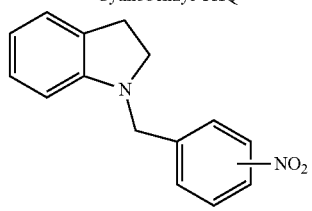
Nitrobenzyl IND

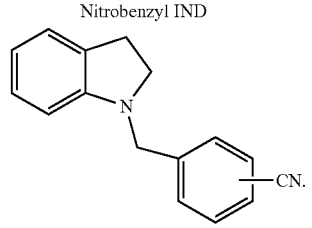
Cyanobenzyl IND

* * * * *

UNITED STATES PATENT AND TRADEMARK OFFICE
CERTIFICATE OF CORRECTION

PATENT NO. : 9,969,690 B2
APPLICATION NO. : 15/452768
DATED : May 15, 2018
INVENTOR(S) : Philip T. Klemarczyk It is certified that error appears in the above-identified patent and that said Letters Patent is hereby corrected as shown below:

In the Specification

Column 2, Line 30 change "$R^1$" to "$R^3$"

Signed and Sealed this
Fifteenth Day of January, 2019

Andrei Iancu
*Director of the United States Patent and Trademark Office*